United States Patent [19]
Mumford et al.

[11] Patent Number: 5,387,504
[45] Date of Patent: Feb. 7, 1995

[54] MONOSPECIFIC ANTIBODIES AND ASSAY SYSTEM FOR DETECTING STROMELYSIN CLEAVAGE PRODUCTS

[75] Inventors: Richard A. Mumford, Red Bank; Michael W. Lark, East Windsor; Ellen B. K. Bayne, Westfield; Lori A. Hoerrner, Scotch Plains, all of N.J.

[73] Assignee: Merck & Co., Inc., Rahway, N.J.

[21] Appl. No.: 954,213

[22] Filed: Sep. 30, 1992

[51] Int. Cl.[6] ............ C12Q 1/37; G01N 33/536; G01N 33/543; G01N 33/573

[52] U.S. Cl. .................. 435/7.1; 435/7.4; 435/23; 436/518; 436/536; 436/547; 424/9; 424/94.67

[58] Field of Search .................. 424/9, 94.67; 530/387.9, 389.2, 806, 389.1, 807, 840; 435/4.1, 960, 975, 7.72, 7.4, 23; 436/503, 504, 545, 547, 548, 804, 811, 518, 536

[56] References Cited

U.S. PATENT DOCUMENTS

4,795,702  1/1989  Blake ........................ 435/7.1

FOREIGN PATENT DOCUMENTS

0044710  1/1982  European Pat. Off. .

OTHER PUBLICATIONS

Heinegard, et al., General Immunological 45, pp. 421–427 (1985).
Farndale, et al., Biochem. Biophys Acta 883; pp. 173–177 (1986).
Flannery, et al., J. Biol. Chem. 267; pp. 1008–1014 (1992).
Fosang, et al., J. Biol. Chem. 266; pp. 15579–15582 (1991).
Hascall and Kimura, Methods Enzymol 82 pp. 769–800 (1982).
Caterson, et al, Articular Cartilage Biochemistry, pp. 59–73 (1986).
Fosang et al, Sep. 25, 1992, The Interglobular Domain of Cartilage Aggrean is Cleaved by PUMP, Gelatinases, and Cathepsin B. J Biol. Chem. 267: 194870–74.
Hughes et al, Aug. 15, 1992, Monoclonal Antibodies Recognizing Protease-Generated Neoepitopes from Cartilage Proteoglycam Degradation. J Biol. Chem 267: 16011–14.
Hui et al, 1983. Monoclonal Antibodies to a Synthetic Fibrin-Like Peptide Bind to Human Fibrin but not Fibrinogen. Sci 222: 1129–32.
Doege et al, Jan. 15, 1991, Complete Coding Sequence and Deduced Primary Structure of the Human Cartilage Large Aggregating Proteoglycan, Aggrecan. J Biol. Chem 266: 894–902.
Hunter, 1979. "Radioimmunoassay", *Handbook of Experimental Immunology. vol. 1. Immunochemistry*, (D. M. Weir, Ed.) Blackwell Scientific Publications, Oxford. pp. 14.1–14.40.

*Primary Examiner*—David Saunders
*Assistant Examiner*—James L. Grun
*Attorney, Agent, or Firm*—John W. Wallen, III; Jack L. Tribble; Paul D. Matukaitis

[57] ABSTRACT

Monospecific antibodies are produced which are specific for fragments of the connective tissue protein aggrecan, generated by specific stromelysin cleavage. These monospecific antibodies are used in an assay system to detect polypeptide fragments of aggrecan, produced by the specific cleavage of aggrecan by stromelysin. The presence of aggrecan polypeptide fragments demonstrates stromelysin activity. Elevations of stromelysin occur in osteoarthritis, rheumatoid arthritis, atherosclerotic lesions, gout, inflammatory bowel disease (IBD), idiopathic pulmonary fibrosis (IPF), certain cancers, joint injuries, and numerous inflammatory diseases. The monospecific antibodies and the assay system are used to quantitate aggrecan polypeptide fragments as a readout of stromelysin activity and to evaluate potential stromelysin inhibitors.

9 Claims, 19 Drawing Sheets

FIG. 14C
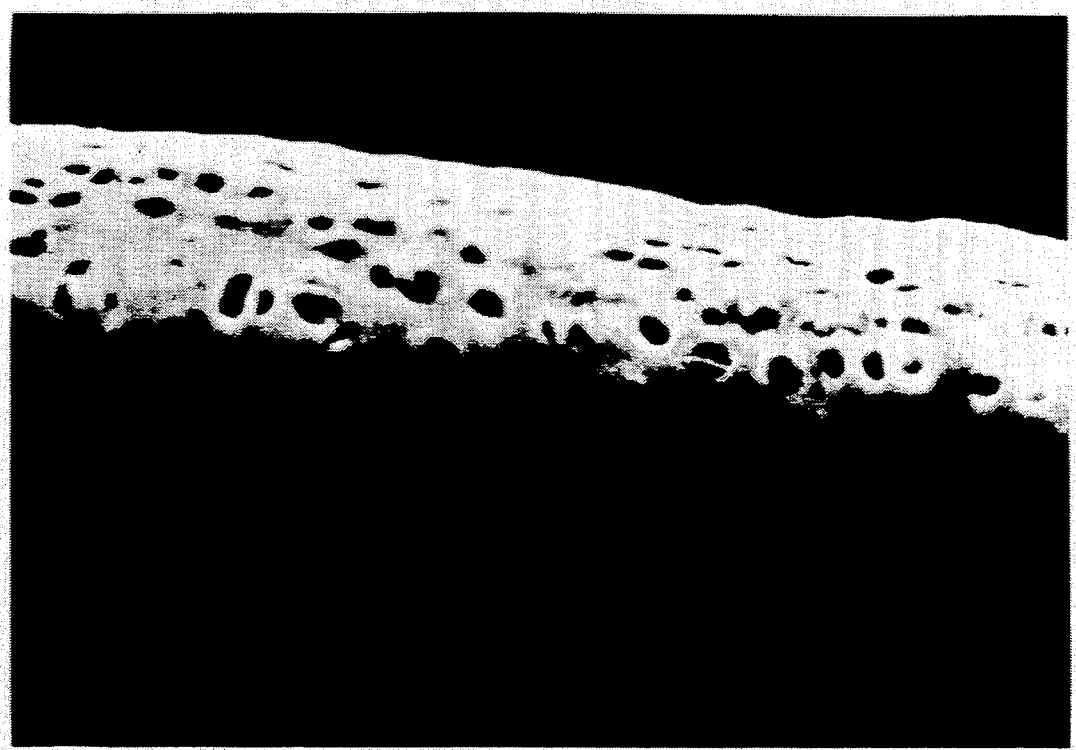
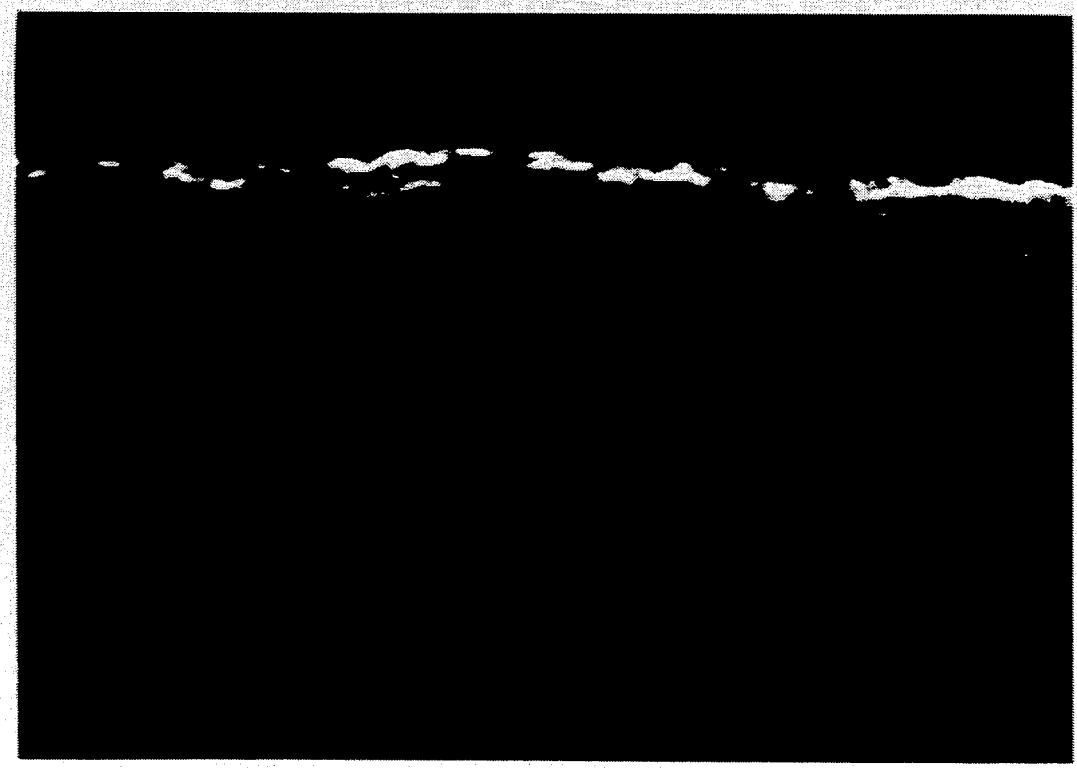
FIG. 14D

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Asp  Ile  Pro  Glu  Asn
    1                      5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Val Asp Ile Pro Glu Asn
1               5

(2) INFORMATION FOR SEQ ID NO:3:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Phe Val Asp Ile Pro Glu Asn
1               5

(2) INFORMATION FOR SEQ ID NO:4:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Asp Ile Pro Glu Asn Phe Phe Gly Val Gly
1               5                   10

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Phe Phe Gly Val Gly Gly
1               5

(2) INFORMATION FOR SEQ ID NO:6:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Phe Val Asn Ile Pro Glu Asn
1               5

(2) INFORMATION FOR SEQ ID NO:7:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Phe Phe Gly Val Gly Gly Glu
1               5

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Cys  Xaa  Phe  Val  Asp  Ile  Pro  Glu  Asn
1                   5
```

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Phe  Phe  Gly  Val  Gly  Gly  Glu  Xaa  Cys
1                   5
```

( 2 ) INFORMATION FOR SEQ ID NO:10:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Tyr  Val  Asp  Ile  Pro  Glu  Asn
1                   5
```

( 2 ) INFORMATION FOR SEQ ID NO:11:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Tyr  Thr  Gly  Glu  Asp  Phe  Val  Asp  Ile  Pro  Glu  Asn
1                   5                        10
```

( 2 ) INFORMATION FOR SEQ ID NO:12:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Tyr  Thr  Gly  Glu  Asp  Phe  Val  Asp  Ile  Pro  Glu  Asn  Phe  Phe  Gly  Val
1                   5                        10                       15
```

( 2 ) INFORMATION FOR SEQ ID NO:13:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Thr  Gly  Glu  Asp  Phe  Val  Asp  Ile  Pro  Glu  Asn
1                   5                         10
```

( 2 ) INFORMATION FOR SEQ ID NO:14:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Gly  Glu  Asp  Phe  Val  Asp  Ile  Pro  Glu  Asn
1                   5                         10
```

( 2 ) INFORMATION FOR SEQ ID NO:15:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Glu  Asp  Phe  Val  Asp  Ile  Pro  Glu  Asn
1                   5
```

( 2 ) INFORMATION FOR SEQ ID NO:16:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Asp  Phe  Val  Asp  Ile  Pro  Glu  Asn
1                   5
```

( 2 ) INFORMATION FOR SEQ ID NO:17:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Tyr  Thr  Gly  Glu  Asp  Phe  Val  Asp  Ile  Pro  Glu  Asp
1                   5                         10
```

( 2 ) INFORMATION FOR SEQ ID NO:18:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:18:

Tyr Thr Gly Glu Asp Phe Val Asp Ile Pro Glu Xaa
1               5                   10

(2) INFORMATION FOR SEQ ID NO:19:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:19:

Tyr Thr Gly Glu Asp Phe Val Asp Ile Pro Asp Asn
1               5                   10

(2) INFORMATION FOR SEQ ID NO:20:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:20:

Tyr Thr Gly Glu Asp Phe Val Asp Ile Pro Glu Gln
1               5                   10

(2) INFORMATION FOR SEQ ID NO:21:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:21:

Tyr Thr Gly Glu Asp Phe Val Asp Ile Pro Glu Ala
1               5                   10

(2) INFORMATION FOR SEQ ID NO:22:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:22:

Tyr Thr Gly Glu Asp Phe Val Asp Ile Pro Ala Asn
1               5                   10

(2) INFORMATION FOR SEQ ID NO:23:

(i) SEQUENCE CHARACTERISTICS:
    (A) LENGTH: 12 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:23:

Tyr Thr Gly Glu Asp Phe Val Asp Ile Ala Glu Asn
1               5                   10

(2) INFORMATION FOR SEQ ID NO:24:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:24:

Tyr Thr Gly Glu Asp Phe Val Asp Ala Pro Glu Asn
1               5                   10

MONOSPECIFIC ANTIBODIES AND ASSAY SYSTEM FOR DETECTING STROMELYSIN CLEAVAGE PRODUCTS

BACKGROUND OF THE DISCLOSURE

The present invention is directed to the development of an antiserum and assay which reflects the in vivo activity of stromelysin in certain animal models as well as in those disease states where stromelysin is thought to play a major and/or central role. In addition, this antiserum and assay allow the evaluation of specific and selective inhibitors of stromelysin in these various diseases. Over 32 million Americans have some type of musculoskeletal disease, and of these, half have osteoarthritis (OA). OA is significantly more prevalent than rheumatoid arthritis (RA). In both RA and OA, there is degradation and loss of cartilage aggrecan and collagen which ultimately results in degradation of the underlying bone. Although the end result is similar for these two diseases, the mechanisms by which these diseases begin and progress appear to be different. RA is an inflammatory disease in which various cytokines such as IL-1 and TNFα have been implicated to stimulate the synovium to proliferate and produce degradative enzymes. On the other hand, OA is a disease which seems to develop from within the cartilage, in which biochemical and biomechanical factors play a major role. For instance, patients with cruciate ligament and meniscal injuries, which destabilize the joint, tend to develop OA at an accelerated rate. In OA, there appears to be synthesis of degradative proteinases by the chondrocytes with synovial hypertrophy and inflammation occuring late in the disease. The degradative proteinase stromelysin (SLN) is common to both OA and RA and may be responsible for the cartilage connective tissue destruction observed in both of these diseases.

SLN is synthesized by chondrocytes and synoviocytes and its synthesis is upregulated by inflammatory cytokines both in vitro and in vivo. Its expression is elevated in animal models of arthritis and in patients with OA, RA and traumatic joint injury. SLN has the capacity to degrade the major cartilage connective tissue elements, including aggrecan, link protein, and type IX collagen. Aggrecan is a large anionic proteoglycan which is responsible for maintaining cartilage's resistance to compression. It is one of the first molecules to be lost from OA cartilage. The release of this molecule appears to be required prior to collagenolytic degradation of type II collagen. 72 kDa and 95 kDa gelatinases are two other members of the metalloproteinase family which have the capacity to degrade aggrecan. However, the expression of the 72 kDa enzyme is not upregulated in either OA or RA. Also, SLN may participate in the activation of both collagenase (CLN) and 95 kDa gelatinase (GEL). Therefore, by inhibiting SLN, we may be able to inhibit and slow the rate of degradation, either directly or indirectly, of all of the major cartilage macromolecules in OA. Presently, general immunological [Heinegard et al., (1985), Scand. J. Clin. Lab Invest., 45, pp. 421–427; Caterson etal., Monoclonal Antibodies Against Cartilage Proteoglycan And Link Protein; in: Articular Cartilage Biochemistry, eds. K.E. Keuttner, R. Schleyerbach and V.C. Hascall, Raven Press, N.Y., 1986, pp. 59–73] and dye based [Farndale et al., (1986), Biochem. Biophys Acta, 882, pp. 173–177] assays are used to quantify aggrecan. These assays do not differentiate degraded from intact aggrecan molecules.

BRIEF DESCRIPTION OF THE DRAWINGS

FIG. 10—FIG. 10A: RIA data is shown which demonstrates the detection and specificity of the assay for SLN-cleaved human aggrecan fragments but not for intact aggrecan.

FIG. 12—FIG. 12A: RIA data is shown which demonstrates the detection and specificity of the assay for SLN-cleaved rabbit aggrecan fragments as compared to 92 kDa gelatinase cleaved rabbit aggrecan fragments.

FIG. 14C: Immunofluorescence data is shown which demonstrates fluorescence in cartilage from a rabbit joint injected intraarticularly with SLN (test cartilage without compound 1 treatment).

FIG. 14D: Immunofluorescence data is shown which demonstrates fluorescence in joint cartilage obtained from a rabbit treated with compound 1 prior to intraarticular injection of the joint with SLN (test cartilage with compound 1 treatment).

Figure 1:
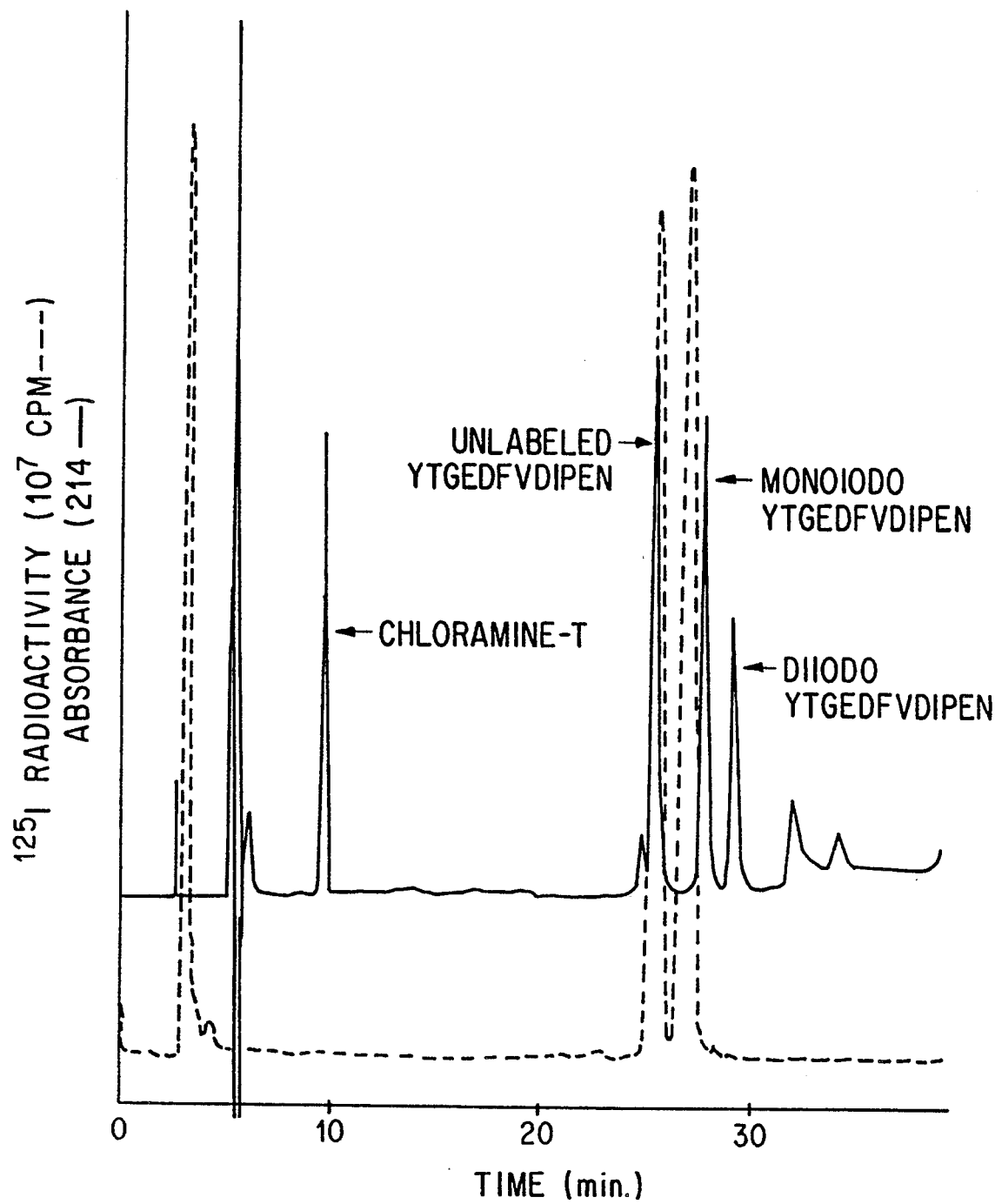
FIG. 1—An HPLC tracing showing the separation of the iodinated synthetic aggrecan probe peptide from non-iodinated peptide.

The non-antibody bound radioactivity was then separated as described above.

SUMMARY OF THE DISCLOSURE

Stromelysin cleavage products such as stromelysin cleaved aggrecan fragments, are measured with a rabbit polyclonal antiserum in either a classical RIA or by classical immunolocalization techniques. The antiserum detects stromelysin-cleaved aggrecan in: (a) SLN digestion of purified rabbit, bovine and human aggrecan in vitro; and (b) cleaved aggrecan in model systems where SLN is injected intraarticularly in vivo (i.e., rabbit knee joint). As a measure of stromelysin activity the antiserum is used to quantify stromelysin-cleaved aggrecan in: (a) models in which endogenous stromelysin synthesis is stimulated by various cytokines (i.e., IL-1 and TNFα); and (b) in various human diseases such as RA and OA. Use of this antibody also allows the evaluation of SLN inhibitors in various pharmocokinetic/pharmacological animal models as well as in various human diseases, such as RA and OA.

DETAILED DESCRIPTION OF THE INVENTION

The present invention is directed to the quantitation and localization of stromelysin cleaved aggrecan fragments as a measure of stromelysin activity. The present invention is also directed to an assay system to evaluate the potency of stromelysin inhibitors in vivo. The quantitation of stromelysin cleaved aggrecan fragments may be useful in the diagnosis of various diseases including but not limited to osteoarthritis (OA) and rheumatoid arthritis (RA), IBD, IPF, gout, atherosclerotic lesions, joint injury and certain cancers. The identification of stromelysin inhibitors may lead to the development of drugs for the treatment of diseases including, but not limited to, OA and RA. More specifically, the present invention is directed to monospecific antibodies which detect stromelysin cleavage products, such as stromelysin-cleaved aggrecan polypeptide fragments.

One way to monitor proteinase activity in situ, is to assay for proteinase mediated degradation products. Since aggrecan is a major cartilage matrix molecule, a SLN substrate, and one of the first molecules to be lost from cartilage in OA, the present invention is focused on developing reagents to quantify SLN-cleaved aggrecan fragments for this purpose. This is the first time that reagents have been developed to qualify defined cleavage sites in extracellular matrix aggrecan molecules. To date, general immunological [Heinegard et al., supra; Caterson et al., supra] and dye based assays [Farndale et al., supra] are used to quantify aggrecan. These assays do not differentiate degraded from intact molecules. The antisera described herein not only recognize degraded and not intact aggrecan, but also recognize aggrecan specifically cleaved by the metalloproteinase stromelysin. Using these antisera, stromelysin cleaved aggrecan molecules can be specifically quantified and localized. It has been shown that SLN cleaves aggrecan between the $Asn^{341}$-$Phe^{342}$ bond within the interglobular domain in the molecule. A synthetic cleavage site-spanning peptide (Asp-Ile-Pro-Glu-Asn-Phe-Phe-Gly-Val-Gly [SEQ. ID. NO.: 4]) is also cleaved by SLN at the expected site. Cleavage of human aggrecan at this site allows for release of the carboxy-terminal fragment ($Phe^{342}$-$His^{2316}$) from the articular cartilage into the synovial fluid. The amino-terminal fragment ($Val^{1}$-$Asn^{341}$) would remain associated with hyaluronic acid in the cartilage or also may be released into the synovial fluid.

As used herein, all amino acid three letter and single letter designations conform to those designations which are standard in the art, and are listed as follows:

| Alanine | Ala | A | Leucine | Leu | L |
| --- | --- | --- | --- | --- | --- |
| Arginine | Arg | R | Lysine | Lys | K |
| Asparagine | Asn | N | Methionine | Met | M |
| Aspartic acid | Asp | D | Phenylalanine | Phe | F |
| Cysteine | Cys | C | Proline | Pro | P |
| Glutamic acid | Glu | E | Serine | Ser | S |
| Glutamine | Gln | Q | Threonine | Thr | T |
| Glycine | Gly | G | Tyrptophan | Trp | W |
| Histidine | His | H | Tyrosine | Tyr | Y |
| Isoleucine | Ile | I | Valine | Val | V |

The assays of the present invention for stromelysin cleavage products are used as a diagnostic tool to demonstrate increased SLN activity in various diseases as well as to monitor the efficacy of specific and selective SLN inhibitors in various animal models and man. In the rabbit IL-1 model SLN inhibitor compound efficacy is evaluated by quantifying fragments of SLN-degraded aggrecan in both articular cartilage and synovial fluid. Therefore, assays to monitor both the amino- and carboxy-terminal SLN-generated aggrecan fragments are useful to characterize SLN inhibitors. In man, it is difficult to assay aggrecan fragments in cartilage as a readout for biochemical efficacy since human articular cartilage cannot be readily obtained from a patient. To monitor SLN inhibitor compound efficacy in man, the carboxy-terminal or amino-terminal aggrecan fragments which are released into synovial fluid, blood, urine or other biological fluids is monitored. The approaches taken in the present invention to develop these assays are described herein.

The stromelysin cleavage site in aggrecan has been identified (J. Biol. Chem., 267, pp. 1008-1014, [1992]) and this site has been confirmed in the 'double globe region' of aggrecan (3. Biol. Chem., 266, pp. 15579-15582, [1991]). The clevage site for stromelysin on aggrecan is Asp Ile Pro Glu Asn/Phe Phe Gly Val Gly [SEQ. ID. NO.: 4]. The peptides around the stromelysin clevage site are synthetically prepared and polyclonal antisera against those peptides are generated to use as immunoreagents to identify these neo-epitopes.

The amino-terminal hyaluronic acid binding domain of aggrecan is extracted from cartilage and a portion of this G1 has the C-terminal amino acids consistent with stromelysin cleavage.

Monospecific antipeptide antibodies are generated which recognize the C-terminus of the amino-terminal fragment (Val$^1$-Asn$^{341}$) and the N-terminus of the carboxy-terminal fragment (Phe$^{342}$-His$^{2316}$) of aggrecan generated by stromelysin cleavage. These antibodies are used to develop radioimmunoassays (RIA) to quantify cleavage of the molecule at this site. Antibodies to the C-terminus (Val Asp Ile Pro Glu Asn$^{341}$ SEQ. ID. NO.: 3) of the anino-terminal fragment have been generated. These antibodies recognizes both SLN-digested human and rabbit aggrecan but not intact human or rabbit aggrecan. Fragments with molecular weight similar to in vitro generated SLN cleaved aggrecan fragments which are recognized by this antibody are isolated from human OA cartilage. This is similar to the sequencing data showing that aggrecan fragments consistent with SLN cleavage can be isolated from human OA cartilage (Example 6). Using this antibody, an RIA has been developed. This assay is used to quantify the amino-terminal aggrecan fragment (Val$^1$-Asn$^{341}$) in human and rabbit cartilage, synovial fluid, blood, urine or other biological fluids. The assay has a limit of detection of 10–20 pM. A series of peptides have been synthesized to determine the specificity of this antiserum. Peptides which are shorter on the C-terminus (i.e. minus the Asn residue) are not recognized (with more than 10,000-fold reduced sensitivity) by the antiserum. Additionally, peptides which are longer on the C-terminus (i.e. containing Phe) are also not recognized by this antiserum. It is necessary to have at least the six amino acid sequence Val-Asp-Ile-Pro-Glu-Asn (SEQ. ID. NO.: 2) for optimal recognition. Substitution of the C-terminal Asn$^{341}$ for Asn-NH$_2$ or for Asp results in a 100 to 1,000-fold loss in recognition. This data demonstrates the necessity of a free carboxyl group on Asn$^{341}$ for optimal recognition by the antiserum and explains why intact aggrecan is not recognized by the antiserum since the free carboxyl of Ash341 is in amide linkage with Phe$^{342}$. Peptides of various length greater than the optimal six amino acids described above are also suitable for use. Congugates of the N-terminal sequence (Phe$^{342}$-Gly$^{347}$) of the carboxy-terminal fragment have been made and injected into rabbits to generate antiserum which is used to quantify the large aggrecan fragment released from the cartilage.

Monospecific antibodies to the SLN-generated aggrecan fragments (AggFgm) are purified from mammalian antisera containing antibodies reactive against AggFgm or are prepared as monoclonal antibodies reactive with AggFgm using the technique of Kohler and Milstein, Nature 256:495–497 (1975). Monospecific antibody as used herein is defined as a single antibody species or multiple antibody species with homogeneous binding characteristics for AggFgm. Homogenous binding as used herein refers to the ability of the antibody species to bind to a specific antigen or epitope, such as those associated with the AggFgm, as described above. The AggFgm specific antibodies are raised by immunizing animals such as mice, rats, guinea pigs, rabbits, goats, horses and the like, with rabbits being preferred, with an appropriate concentration of AggFgm or a synthetic peptide conjugate based on sequences in this fragment either with or without an immune adjuvant.

Preimmune serum is collected prior to the first immunization. Each animal receives between about 0.1 μg and about 1000 μg of AggFgm or peptide conjugate associated with an acceptable adjuvant. Such acceptable adjuvants include, but are not limited to, Freund's complete, Freund's incomplete, alum-precipitate, water in oil emulsion containing Corynebacterium parvum and tRNA. The initial immunization consists of the AggFgm or synthetic peptides based on the C-terminus of the amino-terminal fragment (Val Asp Ile Pro Glu Asn, SEQ. ID. NO.: 2) or the N-terminus of the C-terminal fragment (Phe Phe Gly Val Gly Gly, SEQ. ID. NO.: 5) conjugated to bovine thyroglobulin in, preferably, Freund's complete adjuvant injected at multiple sites either subcutaneously (SC), intramuscular (IM), intraperitoneally (IP) or a combination of the above. The AggFgm or synthetic peptides may also be conjugated to other carrier molecules which include those known in the art, including but not limited to keyhole limpet hemocyanin and BSA. Each animal is bled at prescheduled regular intervals, to determine antibody titer. The animals may or may not receive booster injections following the initial immunization. After the initial immunization, animals with no response or low titers are given booster injections. These animals receiving booster injections are generally given an equal amount of the AggFgm or peptide conjugates in Freund's incomplete adjuvant by the same route. Booster injections are given at about three week intervals until maximal titers are obtained. At about 10 to 14 days after each booster immunization or about hi-weekly after a single immunization, the animals are bled, the serum collected, and aliquots are stored at about −20° C.

Monoclonal antibodies (mAb) reactive with AggFgm or peptide conjugates are prepared by immunizing inbred mice, preferably Balb/c, with AggFgm or peptide conjugates. The mice are immunized by the IP or SC route with about 0.1 μg to about 10 μg, preferably about 1 μg, of AggFgm or peptide conjugates in about 0.5 ml buffer or saline incorporated in an equal volume of an acceptable adjuvant, as discussed above. Freund's complete adjuvant is preferred. The mice receive an initial immunization on day 0 and are rested for about 3 to 30 weeks. Immunized mice are given one or more booster immunizations of about 0.1 to about 10 μg of AggFgm or peptide conjugates in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles medium (DMEM) by procedures know in the art. Supernatant fluids are collected from growth positive wells on about days 14, 18, and 21 and are screened for antibody production by an immunoassay such as solid phase immunoradioassay (SPIRA) using AggFgm or peptide conjugates as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

Monoclonal antibodies are produced in vivo by injection of pristane primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of anti-AggFgm mAb is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of AggFgm in body fluids or tissue and cell extracts.

It is readily apparent to those skilled in the art that the above described methods for producing monospecific antibodies may be utilized to produce antibodies specific for AggFgm. The antibodies are useful in the production of a diagnostic assay system for the detection and measurement of SLN-generated aggrecan fragment levels. Determining the levels of SLN-generated aggrecan fragments is useful in the diagnosis of the development of OA, RA, and other diseases, from analysis of the patients biological fluids. In addition, the antibodies are useful for the immunolocalization of SLN-generated fragments in biopsy/tissue samples. Such analysis allows the determination of sites of SLN activity within extracellular matrix in situ.

To evaluate the efficacy of stromelysin inhibitors, animals are dosed with stromelysin inhibitors and the levels of stromelysin generated aggrecan fragments quantified using the RIA as a monitor of stomelysin activity. A series of animals are injected intraarticularly with stromelysin and the amount of stromelysin generated aggrecan fragments in the cartilage or released into the synovial fluid, blood, or other biological fluid is quantified using the RIA. After enzyme injection, the joints are lavaged with phosphate buffered saline and the cartilage dissected from the bone. The cartilage is extracted with chaotropic buffers [Hascall and Kimura, Methods Enzymol 82: pp. 769–800, (1982)] and the level of stromelysin generated aggrecan fragments in the cartilage extract, synovial lavage, blood, or other biological fluid is quantified using the RIA. A second series of animals are predosed with inhibitor (i.v. or p.o.) and the level of stromelysin digested aggrecan fragments is quantified in the cartilage, synovial fluid or blood as described above. The amount of inhibition is calculated as a percentage of the stromelysin-cleaved fragment generated with inhibition as a proportion of that generated without inhibitor. The same approach is used to quantify the inhibition of stromelysin activity upon intraarticular injection of cytokines. The same assay is used to evaluate inhibitor activity in human RA, OA or other joint pathologies by monitoring the reduction of the stromelysin generated aggrecan fragment in synovial fluid, blood or other biological fluids. This reduction is determined by quantifying the level of the fragment prior to drug treatment followed by quantification of the level after drug treatment. This assay is used to quantify the level of stromelysin generated aggrecan fragments in cartilage from animal models of joint pathology as well as humans with OA, RA or other joint pathologies.

The antiserum generated against the stromelysin-cleaved aggrecan fragment is also used to localize the fragment within cartilage by standard immunolocalization techniques. This approach is used to localize sites of stromelysin activity in situ. In the presence of inhibitor, SLN-generated fragment levels are greatly reduced compared to levels from control animals not injected with inhibitor. By comparing the distribution of the fragment in tissues from animals treated with drug to tissue from animals not treated with drug, the distribution of stromelysin inhibition is localized. This approach is used in tissues from animals injected with stromelysin, animals injected with cytokines to generate stromelysin endogenously, other generalized arthritis animal models or in surgical specimens from patients with OA, RA or other joint pathology.

The following examples are provided as an illustration of the present invention without, however, limiting the same thereto.

Example 1

Peptide Immunogens

Knowing the specific stromelysin cleavage site in human aggrecan allowed the identification of antigenic peptides and peptide probes representing the amino and carboxy termini adjacent to the SLN-cleavage site. The specific amino acid sequence associated with the carboxy terminus of the amino-terminal aggrecan fragment generated by SLN cleavage is Phe-Val-Asp-Ile-Pro-Glu-Asn$^{341}$ (SEQ. ID. NO.: 3) while the sequence associated with the amino terminus of the carboxy-terminal aggrecan fragment generated by SLN cleavage is $^{342}$Phe-Phe-Gly-Val-Gly-Gly-Glu (SEQ. ID. NO.: 7).

Peptide antigens and peptide probes were synthesized using either t-butyloxycatbonyl (t-Boc) or (Fmoc) fluorenylmethoxy-carbonyl chemistries on an ABI 430A peptide synthesizer (Applied Biosystems, Inc.). For t-Boc chemistry, peptide acids were synthesized on standard phenylacetamidomethyl (PAM) resins, while peptide amides were synthesized on methylbenzhydrylamine (MBHA) resins. Syntheses were carried out according to the N-methyl-pyrrolidone (NMP)/HOBT protocols for hydroxybenzyltriazole (HOBT) ester mediated couplings described in detail in the ABI 430A Operators Manual (Applied Biosystems, Foster City, Calif., 1988). Peptidyl resins were cleaved and deprotected with anhydrous hydrogen fluoride in a Protein Research Foundation hydrogen fluoride apparatus or a Multiple Peptide Systems hydrogen fluoride apparatus according to the procedures described in the ABI 430A Operators Manual. Peptides were purified by reversed phase HPLC on a Waters DeltaPak C18 column with an acetonitrile gradient of 2–50% in aqueous 0.1% trifluoroacetic acid (TFA). Purity of individual peptides was assessed by reversed phase HPLC on an Applied Biosystems Spheri-5 C18 column. The structure of the peptides was confirmed by mass spectrometry utilizing either fast atom bombardment or electrospray ionization. For Fmoc synthesis, peptide acids were synthesized on standard Wang resins, while peptide amides were synthesized on Rink amide resins. Syntheses were carried out according to the FastMoc ™ protocols for benzotriazoltetramethyluronium hexafluorophosphate (HBTU) mediated couplings described in detail in the ABI 430A Synthesis Notes (Applied Biosystems, 1992). Peptidyl resins were cleaved and deprotected with TFA according to the procedures described in the ABI 430A Operators Manual. Purification and characterization of the peptides proceeded as described for the t-Boc chemistry. The primary antigen associated with the carboxyl terminus of the amino terminal fragment generated by stromelysin cleavage of human aggrecan Phe$^{335}$-Val-Asp-Ile-Pro-Glu-Asn$^{341}$ (SEQ. ID. NO.: 3) is synthesized with two additional amino acid residues. Cysteine-norleucine is attached to the synthetic peptide Phe-Val-Asp-Ile-Pro-Glu-Asn SEQ. ID. NO.: 3 to give the following antigen: Cys-Nle-Phe-Val-Asp-Ile-Pro-Glu-Asn (SEQ. ID. NO.: 5). The integrity of the carboxyl group on the terminal asparagine residue was unaltered. The cysteine is a linking amino acid because it allows the antigen to be linked or attached to an immunogenic carrier. The norleucine was added as an internal marker to determine the actual number of antigen molecules attached to a single immunogenic carrier. The primary antigen associated with the amino terminus of the carboxy-terminal aggrecan fragment generated by stromelysin, Phe$^{342}$-Phe-Gly-Val-Gly-Gly-Glu$^{349}$ (SEQ. ID. NO.: 7), is synthesized with two additional amino acid residues. The cysteine-norleucine is attached to the synthetic peptide Phe$^{342}$-Phe-Gly-Val-Gly-Gly-Glu SEQ. ID. NO.: 7 antigen to give the following antigen: Phe$^{342}$-Phe-Gly-Val-Gly-Gly-Glu-NleLCys (SEQ. ID. NO.: 9). The cysteine is a linking amino acid which allows the antigen to be linked or attached to an immunogenic carrier. The norleucine was added as an internal marker to determine the actual number of antigen molecules attached to a single immunogenic carrier.

Example 2

Attachment of Antigen to Carrier

Attachment of the antigenic peptides, to the carrier protein was carried out according to a modification of the method of Lerner et al., Proc. Nat. Acad. Sci. USA 78: 3403–3407 (1981) using the heterobifunctional coupling reagent, Sulfo-MBS (Pierce Chemical Co.). The peptide antigen was attached to the carrier bovine-thyroglobulin (TG), by combining 10 mg of TG dissolved in 2.5 ml degassed phosphate buffer, 20 mM, pH 8.0 with 4.2 mg Sulfo-MBS and incubating for 30 minutes at room temperature with stirring. The carrier-coupling reagent mixture was then applied to a disposable PD-10 Sephadex G-25 column (Pharmacia) which had been equilibrated with de-gassed 50 mM phosphate buffer, pH 7.0. A small vial containing 6 micromoles of the purified, lyophilized peptide antigen was placed under the column outlet and the activated TG fraction was eluted into the vial with an additional 3.5 ml of the pH 7.0 buffer. The peptide antigen-activated carrier complex was allowed to react overnight at 4° C. with gentle stirring. The degree of coupling for the VDIPEN SEQ. ID. NO.: 2 peptide antigen was determined by removing an aliquot of the final reaction mixture and passing it through a PD-10 Sephadex G-25 column equilibrated with PBS to remove any remaining free peptide and/or reaction by-products. The degree of coupling for the FFGVG thyroglobulin immunogen complex (SEQ. ID. NO.: 9) (40μg) was determined directly following the dialysis and lyophilization since FFGVG immunogen complex precitates during the coupling reaction. Therefore the procedure described above cannot be used.

An aliquot (50 μl) of the fraction containing the thyroglobulin immunogen complex (determined by A$_{280}$) was evaporated to dryness for amino acid analysis. For amino acid analysis, the samples were hydrolysed using 200 μL of 6.0 N HCl containing 0.1% phenol maintained at 110° C. for 24 hours. The sample was analyzed using a Beckman Model 6300 amino acid analyzer. The analysis showed that there were 25.3 moles of antigen peptide per mole of TG, for the TG-Cys-Nle-Phe-Val-Asp-Ile-Pro-Glu-Asn (SEQ. ID. NO.: 8) immunogen and 78.8 moles of peptide per mole of TG for the Phe-Phe-Gly-Val-Gly-Gly-Glu-Nle-Cys-TG (SEQ. ID. NO.: 9) immunogen.

Synthetic Probes And Specificity Peptides

Antigen probes to determine antibody specificity and to evaluate the presence of and amounts of SLN-cleaved aggrecan fragments were synthesized by the process described above. Antigenic probes used to determine the presence of and amounts of cleavage products were designed to include a tyrosine residue at the terminus distal to the epitope so that the probe could be coupled to $^{125}$I. The initial probe used to determine antibody titer was a synthetic peptide based on the amino acid sequence of Val$^{336}$-Asn$^{341}$ of aggrecan plus an amino terminal tyrosine residue Tyr-Val-Asp-Ile-Pro-Glu-Asn (SEQ. ID. No.: 10). A subsequent probe used to determine antibody titer consisted of a synthetic probe based on the amino acid sequence of Thr$^{331}$-Asn$^{341}$ plus the naturally occurring Tyr residue of 330 Tyr-Thr-Gly-Glu-Asp-Phe-Val-Asp-Ile-Pro-Glu-Asn (FIG. 1) (SEQ. ID. No.: 11). Synthetic peptides used to determine antibody specificity and to demonstrate that specificity resided in the aggrecan Val$^{336}$-Asn$^{341}$ amino acid sequence included those in the following Table 1.

TABLE 1

I. C-TERMINAL TRUNCATIONS: SEQ. ID. No.: 11
1. YTGEDFVDIPEN
2. YTGEDFVDIPE
3. YTGEDFVDIP
4. YTGEDFVDI
5. YTGEDFVD

II. C-TERMINAL EXTENSIONS: SEQ. ID. No.: 11
1. YTGEDFVDIPEN
2. YTGEDFVDIPENF
3. YTGEDFVDIPENFF
4. YTGEDFVDIPENFFG
5. YTGEDFVDIPENFFGV

III. N-TERMINAL TRUNCATIONS: SEQ. ID. No.: 11

| | | | |
|---|---|---|---|
| 1. YTGEDFVDIPEN | 6. FVDIPEN | 11. EN |
| 2. TGEDFVDIPEN | 7. VDIPEN | 12. N |
| 3. GEDFVDIPEN | 8. DIPEN | |
| 4. EDFVDIPEN | 9. IPEN | |
| 5. DFVDIPEN | 10. PEN | |

IV. ADDITIONAL SPECIFICITY STRUCTURES:

| | |
|---|---|
| 1. YTGEDFVDIPED<br>SEQ. ID. No.: 17 | 8. YTGEDFVDIPEA<br>SEQ. ID. No.: 17 |
| 2. YTGEDFVDIPEd-N<br>SEQ. ID. No.: 18 | 9. YTGEDFVDIPAN<br>SEQ. ID. No.: 22 |
| 3. YTGEDFVDIPE(ISO)N<br>SEQ. ID. No.: 18 | 10. YTGEDFVDIAEN<br>SEQ. ID. No.: 23 |
| 4. YTGEDFVDIPDN<br>SEQ. ID. No.: 19 | 11. YTGEDFVDAPEN<br>SEQ. ID. No.: 24 |
| 5. YTGEDFVDIPEQ | |

TABLE 1-continued

SEQ. ID. No.: 20
6. YTGEDFVDIPEQ - amide
SEQ. ID. No.: 20
7. YTGEDFVDIPEN - amide
SEQ. ID. No.: 11

Production of Monospecific Antibody

New Zealand White Rabbits and Hartley outbred guinea pigs were immunized with the immunogen. The initial immunizations employed 333 µg of the immunogen conjugate per 1 ml Freund's complete adjuvant (FCA) given intramuscularly per rabbit. On day 7, animals were again given 333 µg of immunogen in FCA and on day 35 a total of 333 µg of immunogen was given subcutaneously at 6–10 sites. On day 45 the animals were bled, then boosted with 33 µg of immunogen. On day 55, animals were again boosted and 10 days later bled. This boosting and bleeding schedule was continued 3–5 times to obtain an adequate supply of antiserum. Guinea pigs were immunized (67 µg) as described above. All antisera were stored at −20° C.

Radioiodination of the assay probe was accomplished by reaction with Chloramine T. The peptide probe was dissolved in water at a concentration of 220 µg/ml. A 50 µl volume of this solution (containing 11 µg) was added to 10 µl of 0.5 M phosphate (K+) buffer, pH 7.5 and then combined with 2mCi of $^{125}$I Na and 10 µl freshly prepared Chloramine T (0.1 mg/ml) in water. The mixture was allowed to react for 30 seconds and the reaction was stopped with 10 µl of 1 mg/ml NaI plus 1 mg/ml sodium thiosulfate. The radioiodinated probe was purified by HPLC using a Supelco C-8 column (0.4 ×25 cm). The iodinated probe was eluted by a 35 minute 1% per-minute gradient of 99% eluant A-1% eluant B to 36% eluant A-64% eluant B at a flow rate of 1 ml per minute. Eluant A consisted of 0.1% trifluoroacetic acid in water and eluant B consisted of 0.1% trifluoroacetic acid in acetonitrile. The purification of the monoiodinated Tyr-330–341 peptide is shown in FIG. 1.

Example 3

Radioimmunoassay For Stromelysin Cleavage Products General Immunoassay Protocol The assay was conducted in a total volume of 300 µl of Dulbecco's calcium-and-magnesium-free phosphate buffered saline supplemented with 0.1% gelatin, 0.01% thimerasol and 1.0 mM EDTA. To 100 µl of buffer or sample were added 100 µl of antiserum and allowed to incubate overnight at 4° C. The following day the radioactive probe in the same buffer was prepared such that about 30,000 cpm were added to each sample or control. The assay mixture was incubated overnight at 4° C. and terminated by the addition of 0.3% dextran-coated charcoal. After sedimentation of the charcoal by centrifugation, the supernatant fluid was decanted and the amount of radioactivity determined.

Antiserum titers were determined in this protocol by varying the dilution of the antiserum added in the 100 µl volume. The antibody dilution used in competition experiments was selected to yield approximately 30% binding of the radioactive probe. Antibody sensitivities were determined using samples containing different known amounts of the synthetic probe peptide (Val-Asp-Ile-Pro-Glu-Asn). SEQ. ID. NO.: 2 Specificities were determined by comparing the displacement curve generated by (Val-Asp-Ile-Pro-Glu-Asn) SEQ. ID. NO.: 2 peptide to those generated by putative cross-reactive peptides. The concentration of peptide in unknown samples was determined by comparing control antibody binding of probe obtained in the presence of sample to a standard curve generated using known concentrations of the standard peptides, Tyr-Val-Asp-Ile-Pro-Gly-Asn SEQ. ID. NO.: 10 and Tyr-Thr-Gly-Glu-Asp-Phe-Val-Asp-Ile-Pro-Glu-Asn SEQ. ID. NO.: 11.

Determination of Antibody Binding

Figure 2:
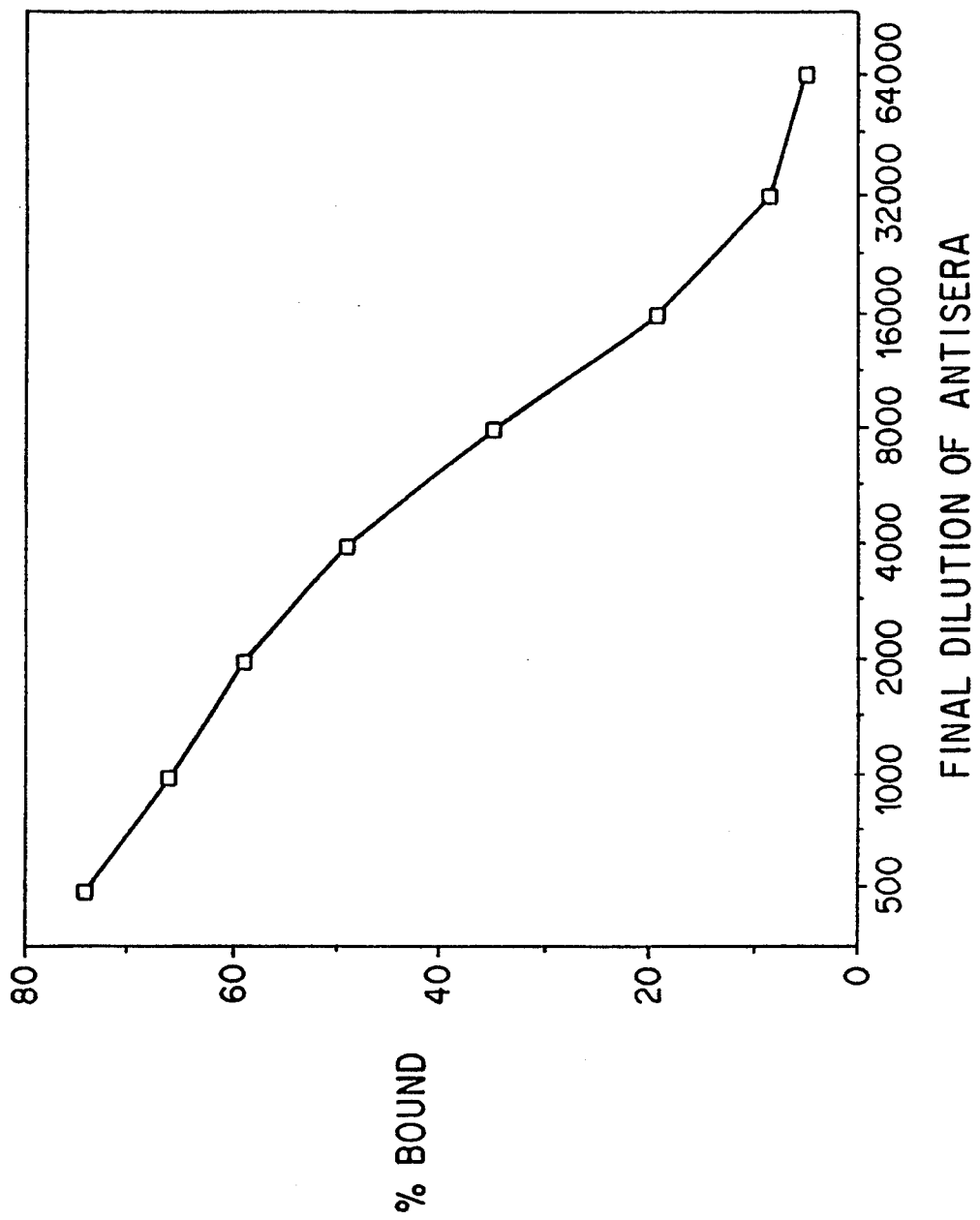
FIG. 2—RIA data is shown for various dilutions of the monospecific anti-VDIPEN antisera.
Figure 3:
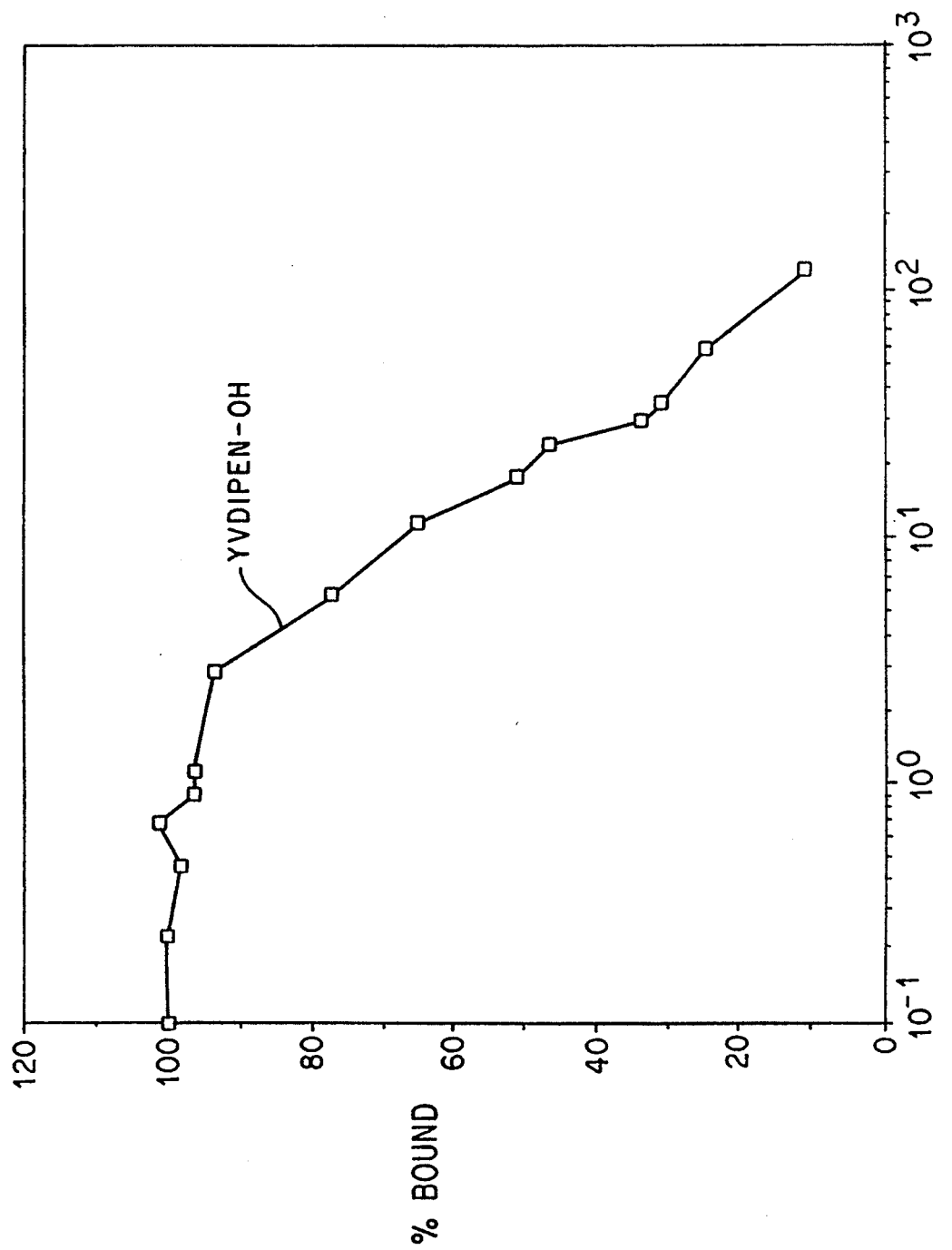
FIG. 3—Demonstration of the sensitivity of the monospecific anti-VDIPEN antisera by measuring its ability to inhibit binding to a radio-labelled peptide by the addition of unlabelled peptide.

The antibody titer for the most active rabbit antisera, against the peptide antigen of was determined using a radioimmunoassay. The antiserum was diluted in assay buffer, see FIG. 2, with dilutions ranging from 1:500 to 1:64,000 per 100 µl. The diluted antiserum was contacted with $^{125}$I-Tyr-Val-Asp-Ile-Pro-Glu-Asn SEQ. ID. NO.: 10 radiolabeled probe. The radioactive probe was diluted in assay buffer to yield approximately 30,000 cpm per 100 µl aliquot. The assay volume was made up to 300 µl by the addition of 100 µl assay buffer. All determinations were made in duplicate.

After overnight incubation at 4° C., antibody-bound and unbound radioactive probe were separated by adsorption of the unbound probe onto dextran-coated charcoal or by adsorption of the bound probe to a complex of normal rabbit serum and goat anti-rabbit IgG. For the charcoal solution Dextran-coated charcoal was prepared by suspending activated charcoal, USP, at a 3%, w/v, concentration in 10 mM phosphate buffer, pH 7.5, containing 0.25%, w/v, T-70 dextran, 70,000 average molecular weight (Pharmacia). The mixture was allowed to stand overnight, sedimented by centrifugation, washed once in dextran-containing phosphate buffer as above, then resuspended to a 3% concentration in the dextran-containing assay buffer. Immediately prior to use in the assay, the dextran-coated charcoal was diluted 10-fold in Dulbecco's PBS and 1 ml is added to each assay tube. After an incubation period of 10 minutes in an ice/water slurry, the charcoal was sedimented by centrifugation at 3,000×g for 10 minutes and the supernatant fluid was decanted and counted in a gamma counter. The assay included charcoal-free controls (to which 1 ml PBS was added), for determination of total counts and antibody-free controls for determination of non-specific binding. For the goat anti-rabbit IgG/normal rabbit IgG (GARGG/NRS) procedure (double antibody) 200 µl of GARGG/NRS complex was added to each tube. The GARGG/NRS complex was prepared by mixing 2 ml of goat anti-rabbit serum with 1.0 ml of normal rabbit serum and allowed to precipitate (2 hours—overnight at 4° C.), then washed 3 to 4 times to eliminate serum components. The pellet was resuspended to 50 ml with RIA buffer and vortexed vigorously. After adding 200 µl of this suspension to each assay tube, the tubes were allowed to stand at room temperatures for 90 minutes. The assay mixture was centrifuged at 3000×g for 15 minutes and the supernatant aspirated. The amount of radioactivity in the pellet was quantitated by gamma counter. The total counts, nonspecific bound counts (tubes without antibody) and the 100% bound counts (tubes with antibody alone) were determined. The percent specific binding at each antiserum dilution was determined by subtracting the antibody-free, or nonspecific binding value from each value for antibody binding, and dividing by the total counts in the system.

Determination of Antibody Sensitivity

Figure 8:
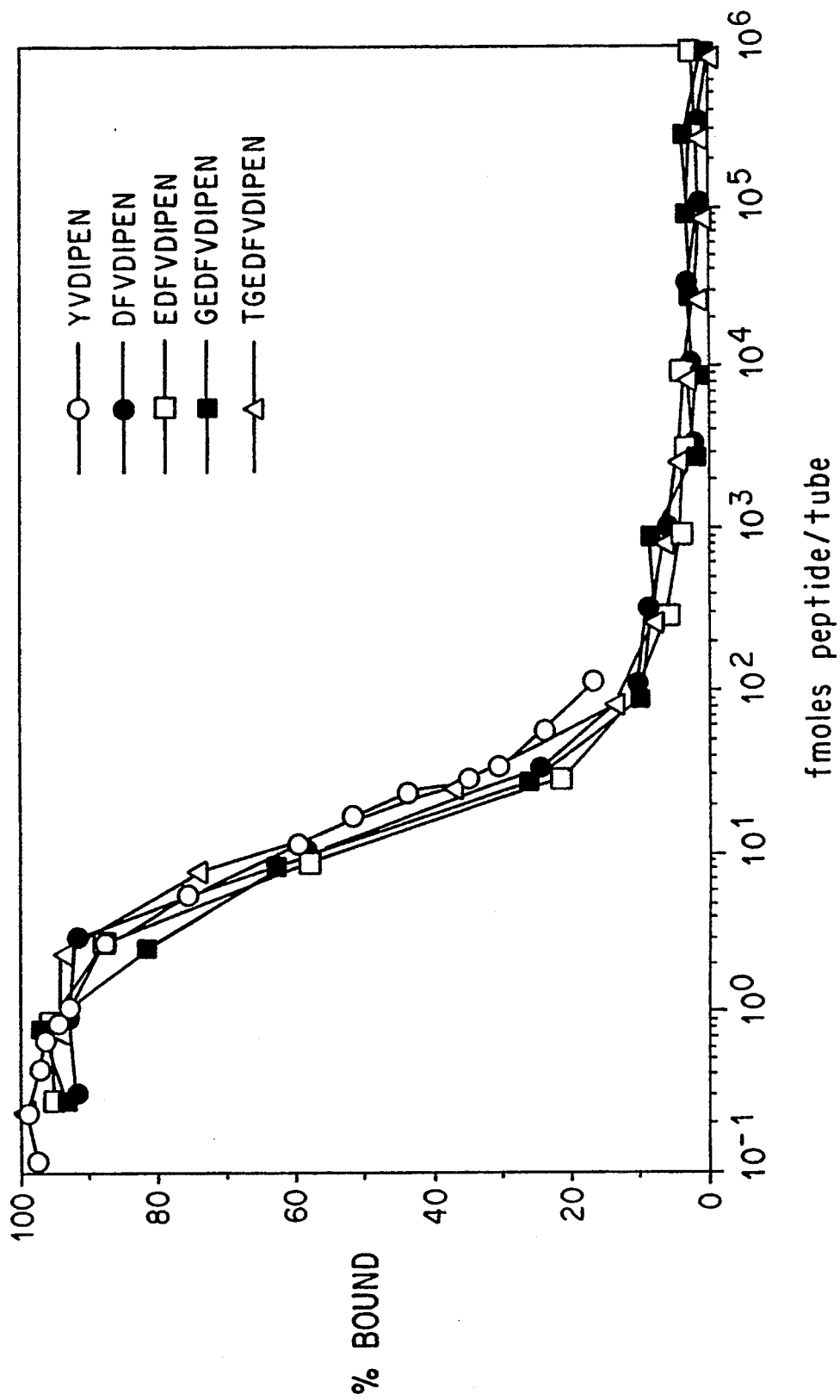
FIG. 8—Demonstration of the specificity of monospecific anti-VDIPEN antisera to recognize six different peptides corresponding to amino terminal extended, SLN-cleaved aggrecan fragments.
Figure 9:
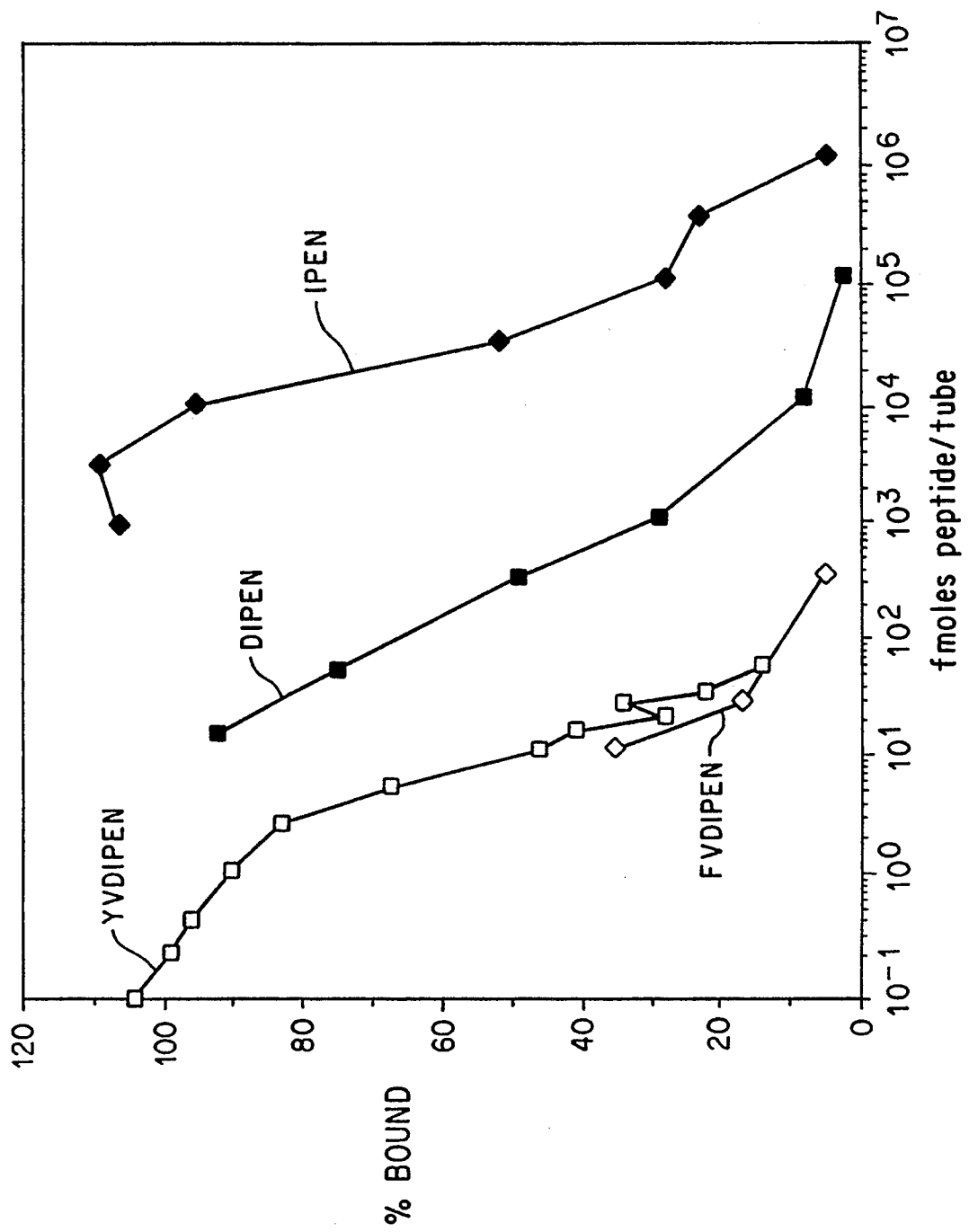
FIG. 9—Demonstration of the specificity of monospecific anti-VDIPEN antisera to recognize Phe-Val-Asp-Ile-Pro-Glu-Asn SEQ. ID. No.: 3 peptides truncated on the amino-terminus.

Antibody sensitivity was determined by evaluating the ability of various concentrations of unlabelled probe to inhibit binding to the radioactively labelled probe. The antiserum, was diluted in the assay buffer, to a concentration of 1:3000 and 100 µl was used in each sample of the assay. The unlabelled probe, Tyr-Val-Asn-Ile-Pro-Glu-Asn was diluted in assay buffer to give final concentrations of $10^{-16}$ to $10^{-13}$ moles, per 100 µl. The unlabelled probe and antibody were allowed to react overnight at 4° C.. The following day the radioactive probe $^{125}$I-tyrosyl-Val-Asp-Ile-Pro-Glu-Asn SEQ. ID. NO.: 6 (30,000 cpm/100 µl) was added and allowed to react overnight at 4° C. The assay included antibody-free controls to determine non-specific binding and controls containing antibody plus probe, to determine the control level of binding. All determinations were made in duplicate. The assay samples and controls were processed and counted using either the charcoal or double antibody procedure. Percent control binding was determined by calculating the average cpm for the duplicate samples at each concentration of probe, subtracting the average non-specific binding cpm, and dividing the results by the antibody only counts. The results are shown in FIG. 8.

Determination of Antibody Specificity

Antibody specificity was determined by evaluating the ability of unlabelled peptides, specificity probes, of varying length, see Table I, to inhibit the binding of the $^{125}$I-Tyr-Val-Asp-Ile-Pro-Glu-Asn SEQ. ID. NO.: 10 radioactive probe. Rabbit antiserum prepared against the Val-Asp-Ile-Pro-Glu-Asn SEQ. ID. NO.: 2 immunogen based on the stromelysin cleavage site in aggrecan described in Example 1 was diluted in assay buffer, at a dilution of 1:3000. The specificity peptides of Table I were diluted in assay buffer at concentrations ranging from approximately $10^{-6}$ to $10^{-13}$ moles peptide/tube. One hundred µl of each dilution was added to 100 µl of antiserum and allowed to react overnight at 4° C. The following day 100 µl of radioactive probe. The radioactive probe $^{125}$I-Tyr-Val-Asp-Ile-Pro-Glu-Asn (SEQ. ID. NO.: 10) (30,000 cpm in 100µl was allowed to react overnight at 4° C. The assay included antibody-free controls used to determine non-specific binding and controls containing antibody plus probe to determine the control level of probe binding. All determinations were made in duplicate. After the second overnight incubation at 4° C., non-antibody-bound radioactive probe was separated as described above using the double antibody procedure. The assay included charcoal-free or GARGG/NRS-free controls, to which 1 ml of PBS was added, for the determination of total counts.

The antibody-free control and the zero-peptide antibody control are counted to determine the 0% bound and the 100% bound values respectively. Radioactivity was determined using a gamma counter and standard techniques known in the art. The samples containing the test peptides are then counted and the amount of radioactivity associated with the antibody-free control subtracted from each. The resulting net counts are divided by the net counts in the antibody-only control to determine the percent bound in the presence of each amount of peptide. The following FIGS. 4 through 9 show the cross-reactivity for a variety of synthetic peptides related to the stromelysin cleavage site Asn$^{341}$-Phe$^{342}$. The results are presented in FIGS. 4 to 9.

Immunoassay Protocol For The Determination Of VDIPEN Epitope Containing Peptide Concentration In Unknown Samples The radioimmunoassay was conducted in a total volume of 300 µl with all dilutions carried out in assay buffer. Standard solutions were prepared at concentrations in the range of $1 \times 10^{-9}$ to $10^{-16}$ moles/tube. The assay included antibody-free controls to measure non-specific binding, and controls containing antibody and probe without added standard samples or unknown samples to determine the control level of peptide binding. To 100 µl of buffer, standard sample or unknown was added, 100 µl of specific antiserum from Examples 2 and 7, diluted 1:9,000 in assay buffer. The reaction was allowed to incubate overnight at 4° C. The following day the probe peptide $^{125}$I-Tyrosyl Val-Asp-Ile-Pro-Glu-Asn SEQ. ID. NO.: 10 (30,000 cpm/100 µl) was added and was incubated overnight at 4° C. The non-antibody bound radioactivity was then separated as described above. Radioactivity was determined using a gamma counter and standard techniques known in the art.

The antibody-free control and the zero-peptide antibody control were counted to determine the 0% bound and 100% bound values respectively. The assay standards are then counted and divided by the antibody control to determine the percent bound and a standard curve was generated. When the percent bound is plotted as a function of the logarithm of the amount of peptide in the standard, a sigmoidal curve is generated which is close to linear between the limits of 80% bound and 20% bound. Unknowns are counted, their percent of control calculated and they are compared to the standard curve to determine the amount of peptide present in the sample. Only those unknowns with values between 80% and 20% of control binding are considered valid.

Example 4

Assay Procedure

Figure 4:
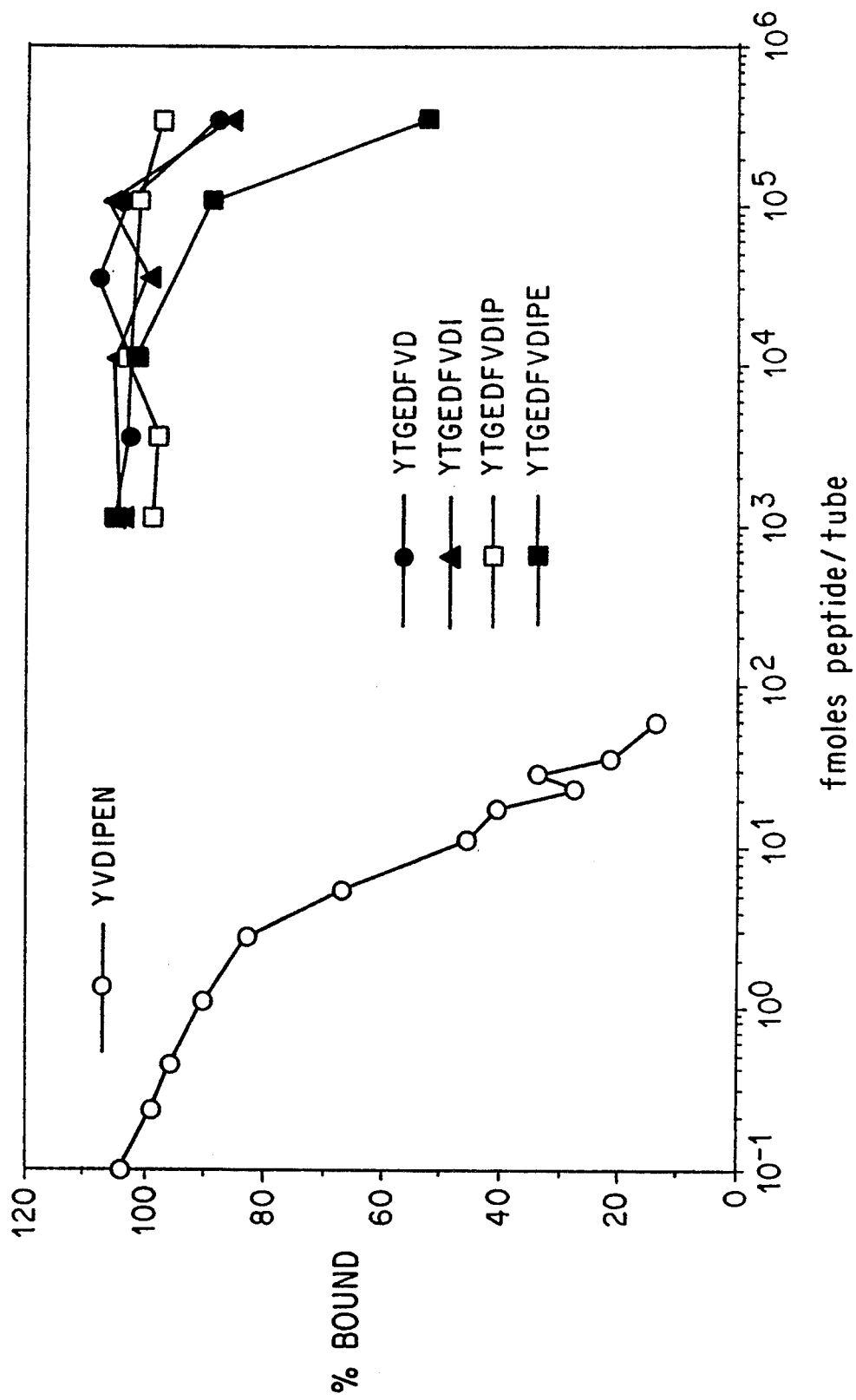
FIG. 4—Demonstration of the specificity of monospecific anti-VDIPEN antisera showing the requirement for the C-terminal Ash of the peptide sequence Asp-Ile-Pro-Glu-Asn SEQ. ID. NO.: 1 for recognition.
Figure 5:
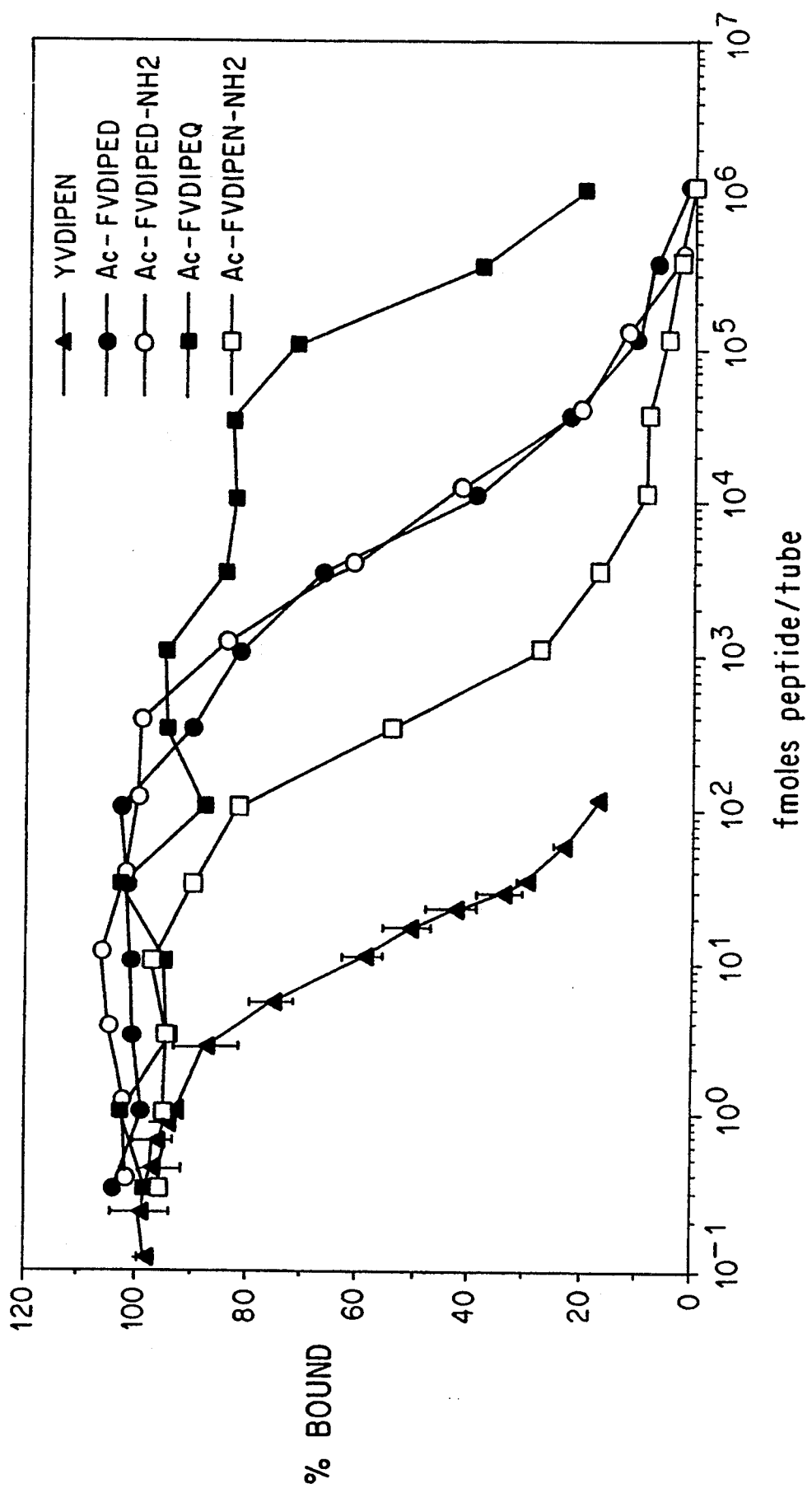
FIG. 5—Demonstration of the specificity of monospecific anti-VDIPEN antisera by showing either the substitution of Ash$^{340}$ or modification to an amide side chain drastically reduces its ability to bind to the antibody.
Figure 6:
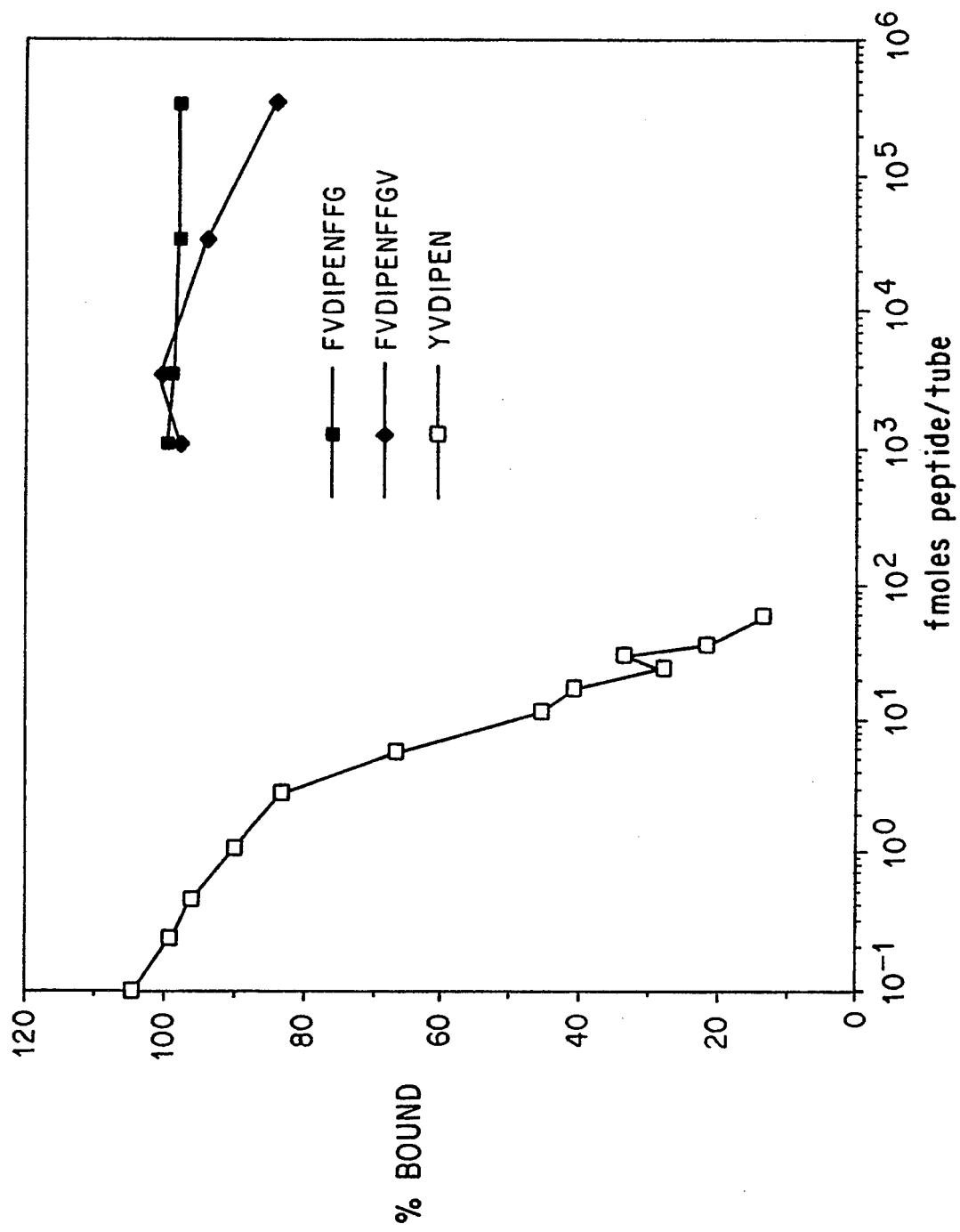
FIG. 6—Demonstration of the specificity of monospecific anti-VDIPEN antisera showing that the antibody does not recognize peptides extended across the agreccan stromelysin cleavage site.
Figure 7:
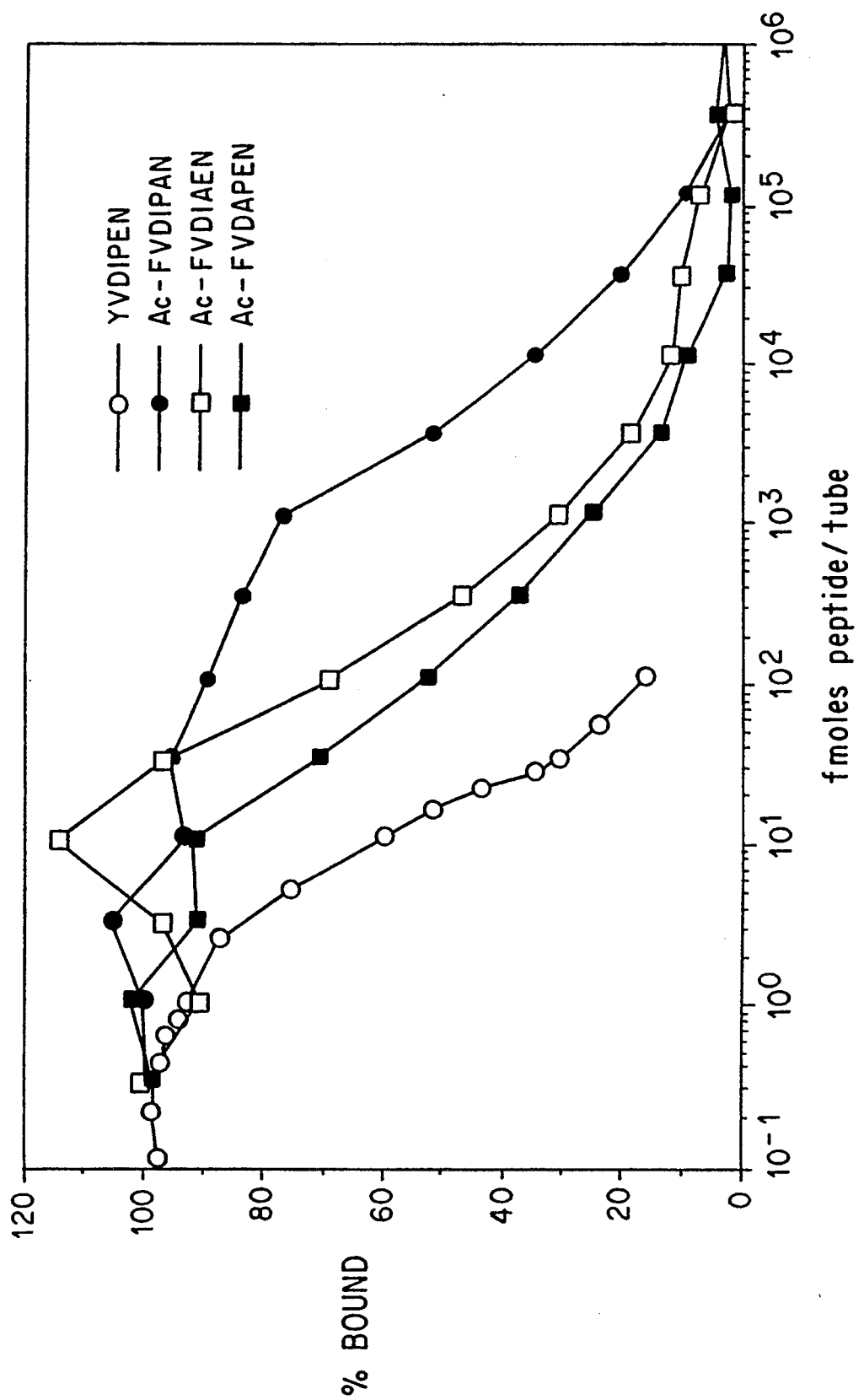
FIG. 7—Demonstration of the specificity of monospecific anti-VDIPEN antisera showing that there is loss of recognition by anti-VDIPEN antisera if there are substitutions of any of the amino acids in Ile-Pro-Glu- of the sequence Val-Asp-Ile-Pro-Glu-Asn SEQ. ID. NO.: 2.
Figure 10A:
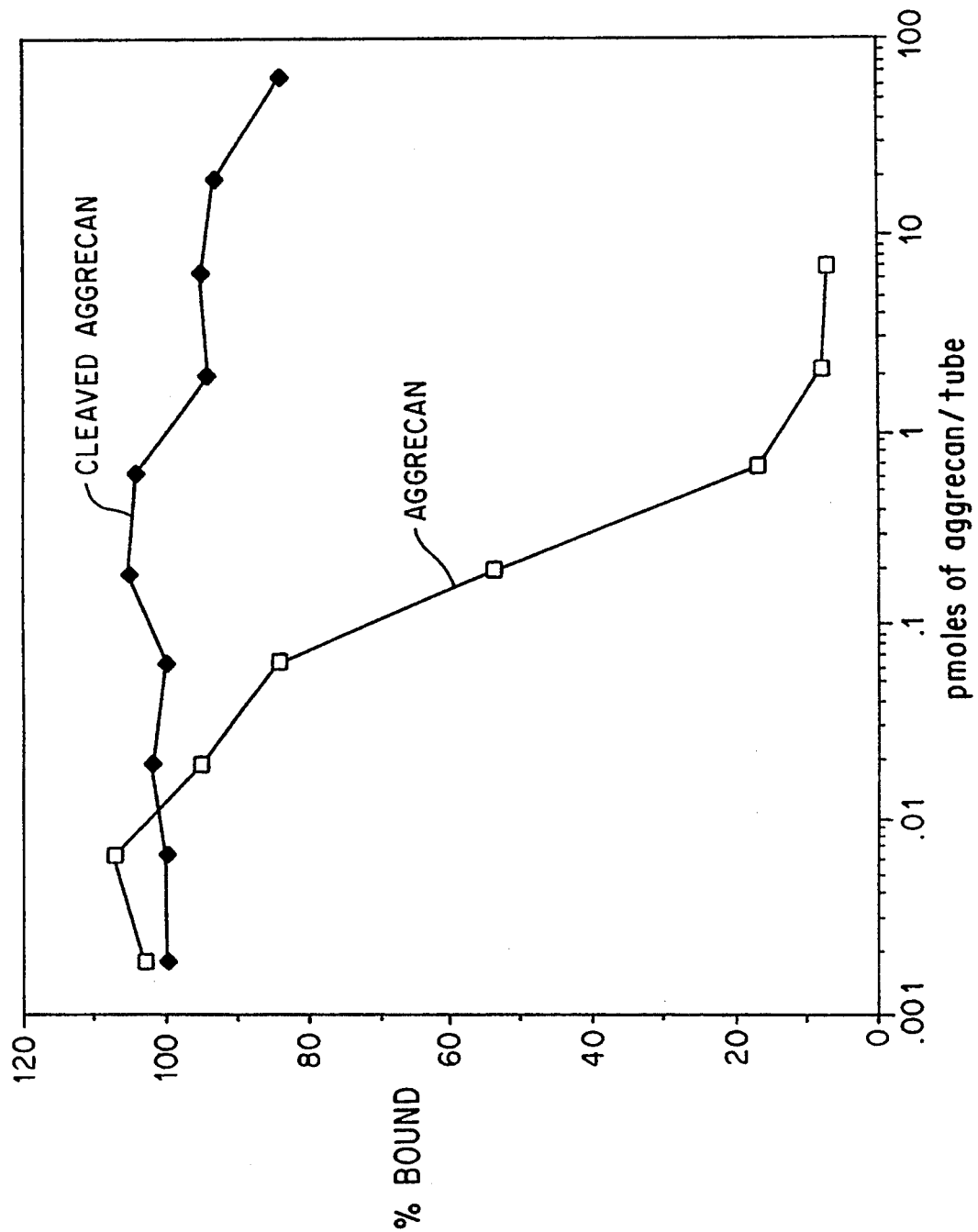
Figure 10B:
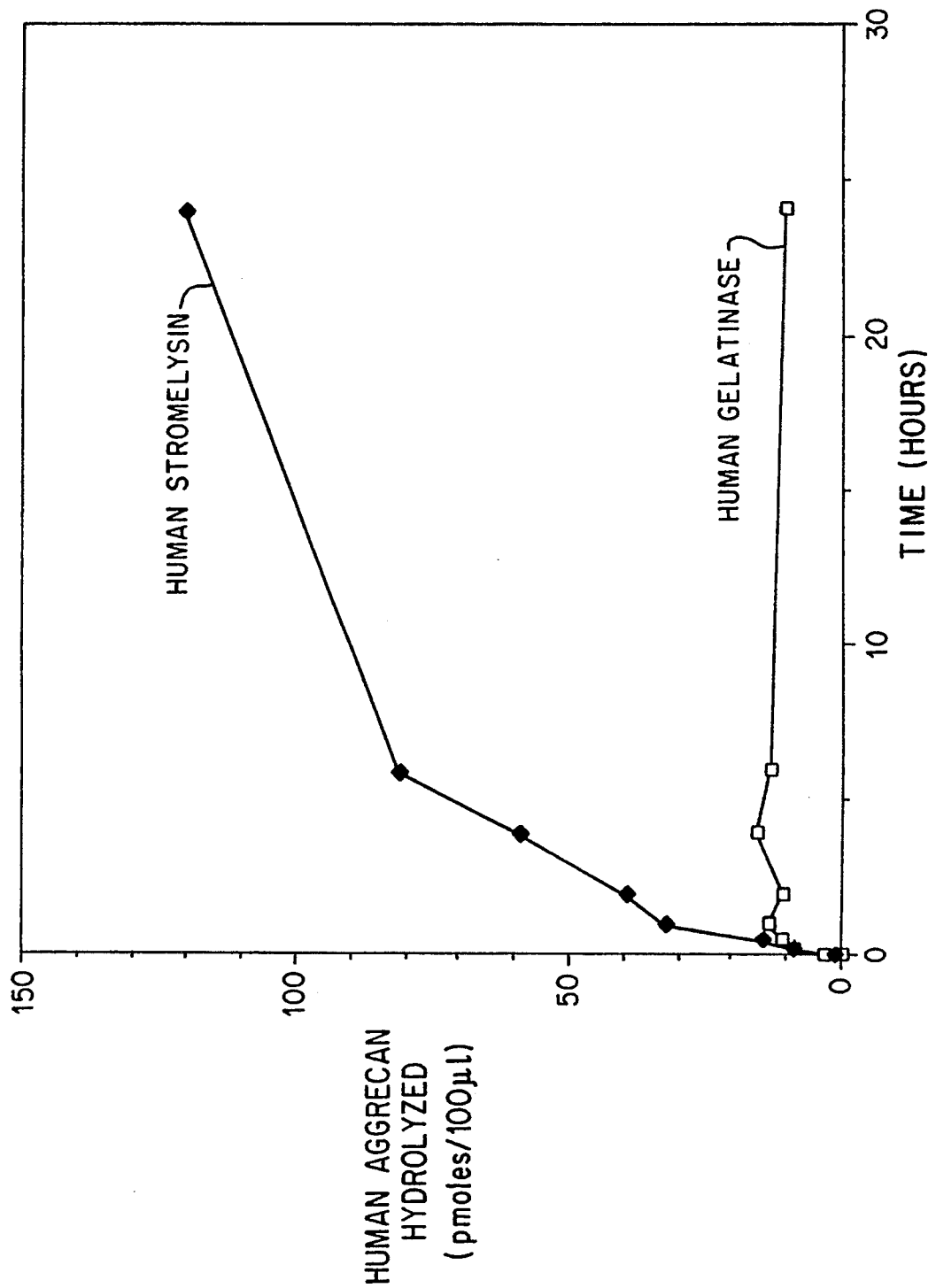
FIG. 10B: RIA data is shown which demonstrates the detection and specificity of the assay for SLN-cleaved human aggrecan fragments but not 72 kDa gelatinase cleaved human aggrecan fragments.
Figure 11:
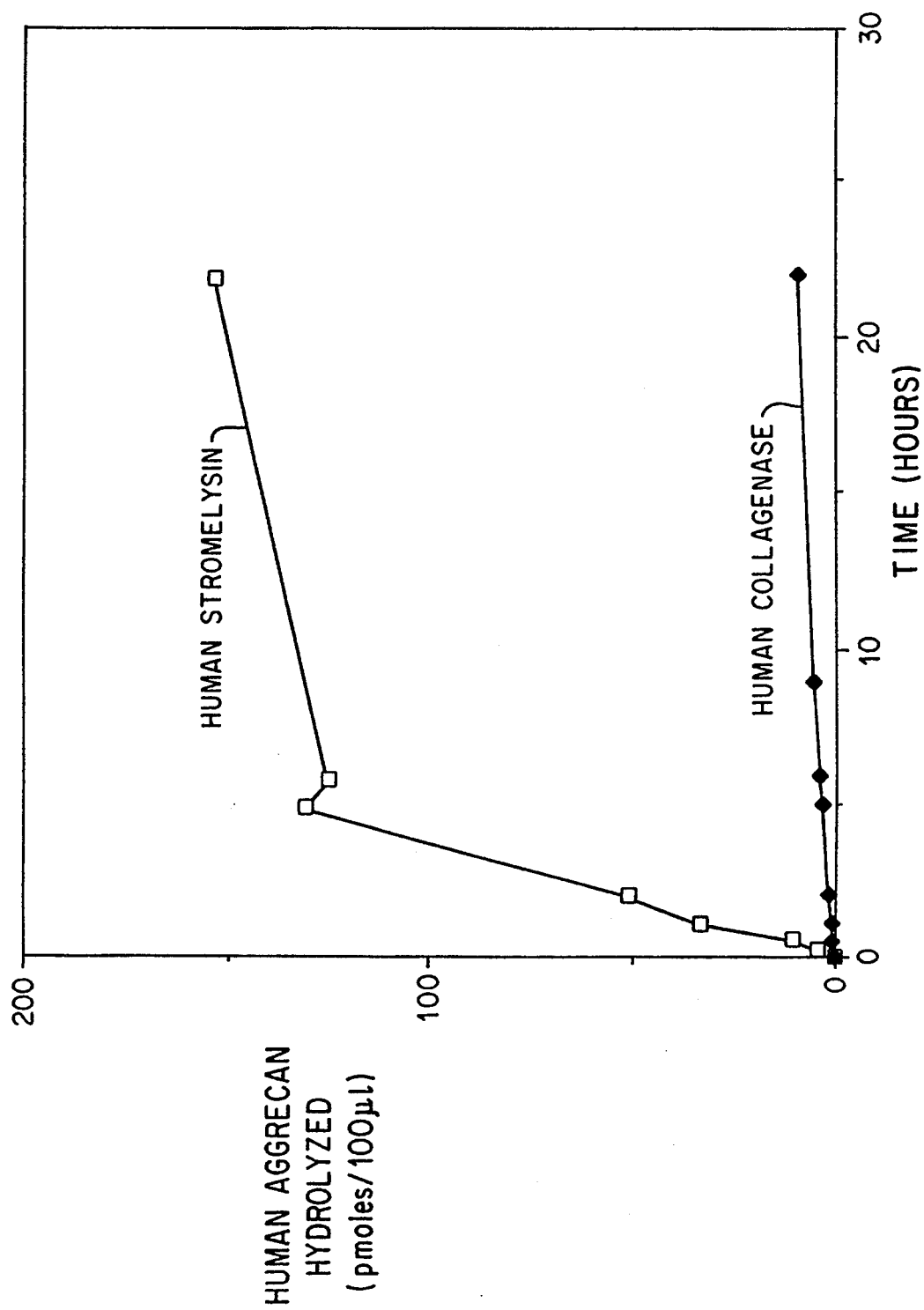
FIG. 11—RIA data is shown which demonstrates the specificity of the assay for SLN-cleaved human aggrecan compared with CLN-cleaved human aggrecan.
Figure 12A:
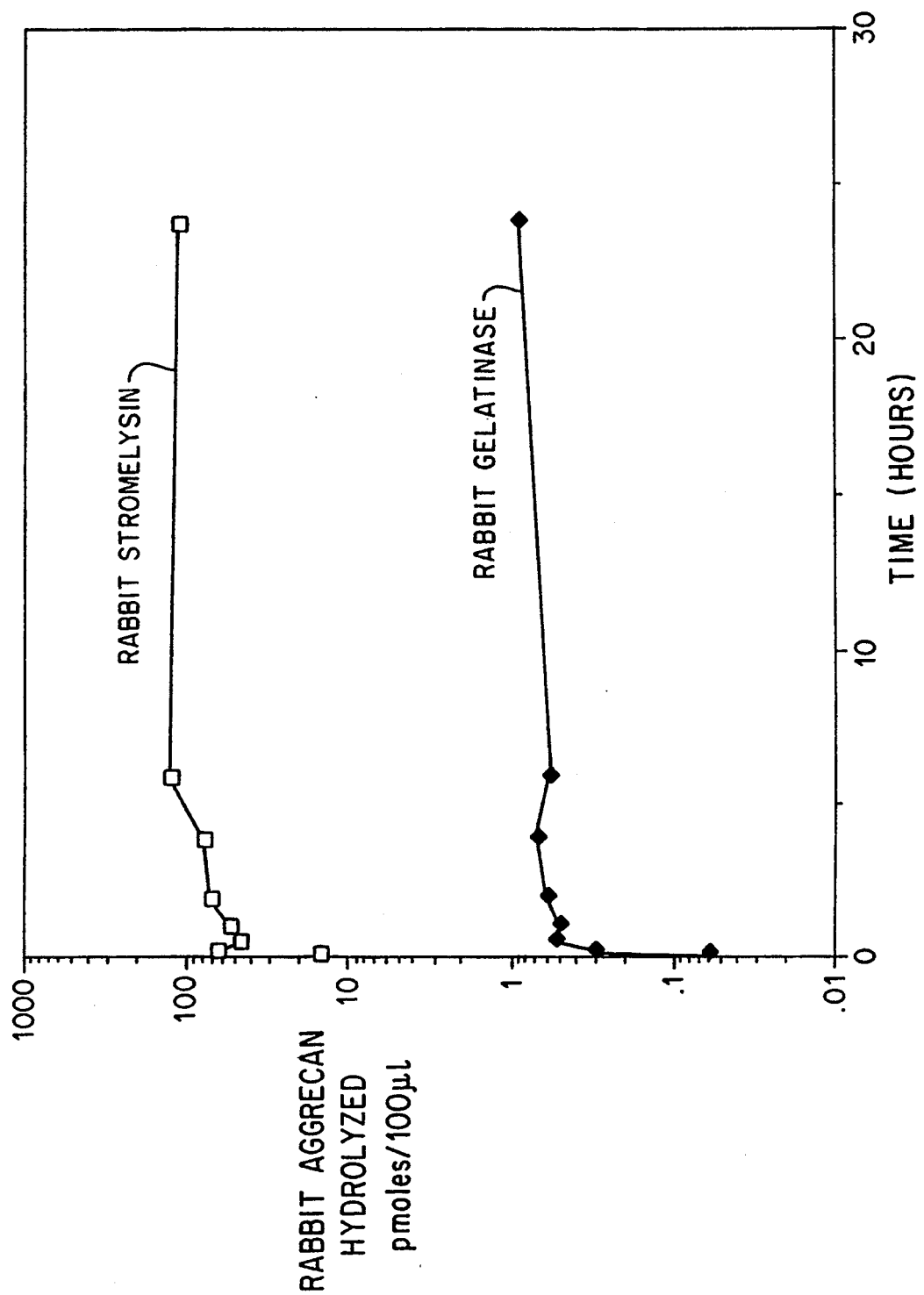
Figure 10C:
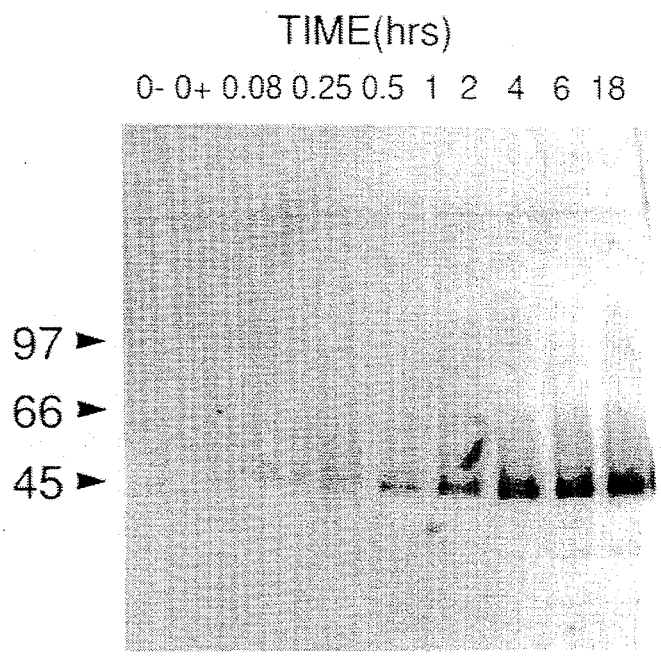
FIG. 10C: A Western blot is shown which demonstrates the detection of SLN-cleaved human aggrecan fragments following SDS-PAGE.
Figure 10D:
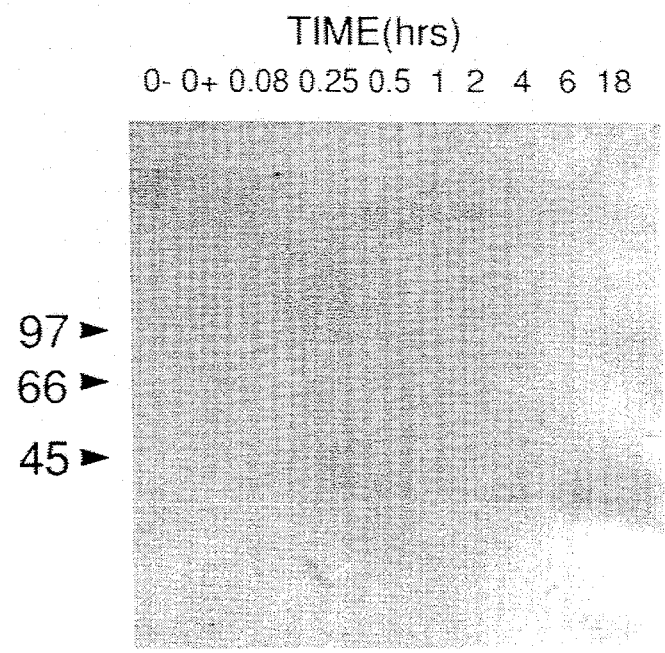
FIG. 10D: A Western blot is shown which demonstrates the detection of human 72 kDa gelatinase-cleaved human aggrecan fragments following SDS-PAGE.
Figure 12B:
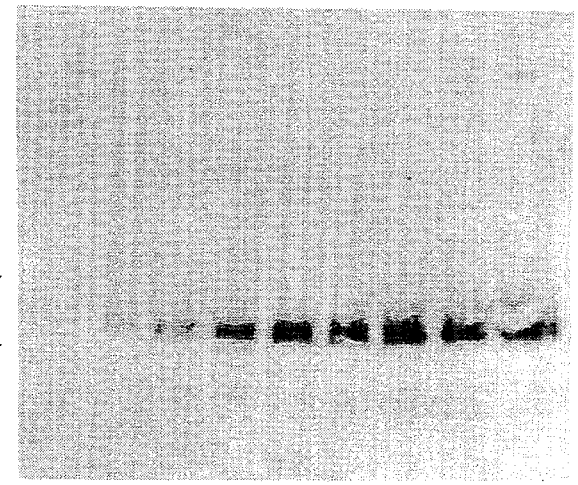
FIG. 12B: A Western blot is shown which demonstrates the detection of SLN-cleaved rabbit aggrecan fragments following SDS-PAGE.
Figure 12C:
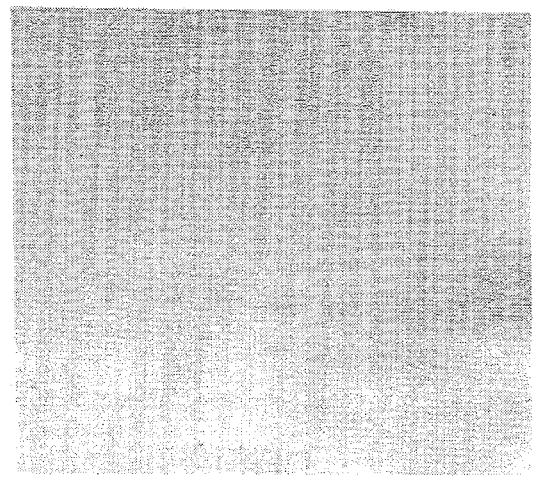
FIG. 12C: A Western blot is shown which demonstrates the detection of rabbit 95 kDa gelatinase-cleaved rabbit aggrecan fragments following SDS-PAGE.

The RIA has been used to quantify stromelysin cleavage of both human (FIGS. 10A-B and 11) and rabbit (FIG. 12A) aggrecan. Human and rabbit aggrecan were extracted from articular cartilage [Hascall and Kimura, (1982), Methods Enzymol. 82, pp. 769-800] and aggregated with hyaluronic acid. The human aggrecan aggregate (3.7 mg, 1.85 nmoles) was digested with human SLN (10µg, 0.182 nmoles) in a total volume of 1 ml. The rabbit aggrecan aggregate (5 mg, 2.5 nmoles) was digested with rabbit SLN (13.5 µg, 0.26 nmoles) in a total volume of 970 µl. At each time point 100 µl aliquots of sample was removed and brought to 10 mM with EDTA to inhibit enzyme activity. The aliquots were evaluated for VDIPEN SEQ. ID. NO.: 2 epitope by RIA (FIGS. 10A-B). With no addition of enzyme, there was no detectable epitope in the sample. There was a time dependent increase in the epitope upon the addition of the enzyme. Less than 10% of the signal was generated when two other closely related metalloproteinases, collagenase (FIG. 11) or gelatinase (FIGS. 10B and 12A) were added to aggrecan (FIG. 4). Generation of the epitope was also monitored by Western blotting using the antiserum against the stromelysin-cleaved human (FIG. 10C-D) and rabbit (FIGS. 12B-C) aggrecan fragments. When the antiserum was preadsorbed with the antigenic peptide Tyr-Val-Asp-Ile-Pro-Glu-Asn, SEQ. ID. NO.: 10 the Western blot signal was eliminated. When the antiserum was preadsorbed with the peptide based on the sequence spanning the SLN cleavage site in aggrecan, Val-Asp-Ile-Pro-Glu-Asn-Phe-Phe-Gly-Val-Gly-$NH_2$ SEQ. ID. NO.: 4 there was little effect on the Western blot signal. When the antiserum was preadsorbed with antigenic peptide with the C-terminal Asn amidated, Tyr-Val-Asp-Ile-Pro-Glu-Asn-$NH_2$, SEQ. ID. NO.: 10 there was a clear reduction in the signal, but not complete elimination. Together, these results indicate that the antiserum requires the C-terminal Asn (not amidated) for optimal recognition, and the Western blot signal is specific for Tyr-Val-Asp-Ile-Pro-Glu-Asn. SEQ. ID. NO.: 10

Example 5

Inhibitor Screening Assay

Figure 15:
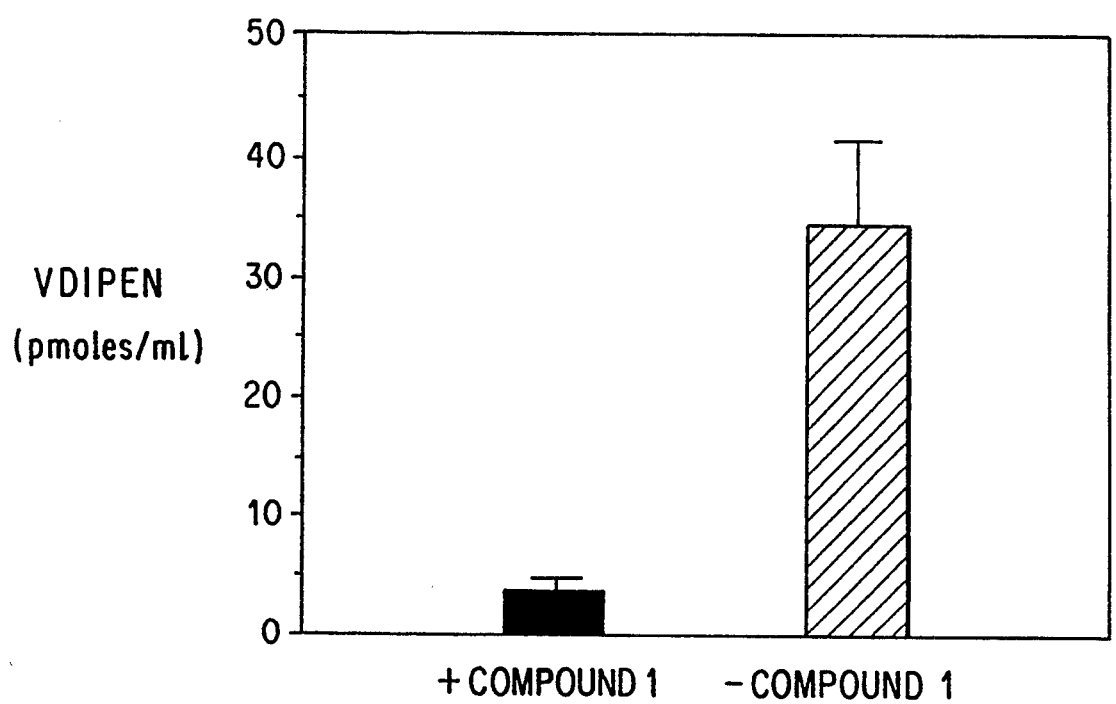

Three rabbits were dosed at 30 mpk i.v. with the stromelysin inhibitor compound 1, (N-[1(R)-carvoxy-ethyl-alpha-(S)-(2-phenyl-ethyl)-glycine-(L)-leucine N-phenylamide) 15 minutes prior to intraarticular stromelysin injections. Three additional control animals were dosed with vehicle alone. All animals were injected intraarticularly in one hind limb joint with 100μg of stromelysin while the other hind limb joint was injected with enzyme buffer. After 1 hour the animals were sacrificed and the joints lavaged with 1 ml of phosphate buffered saline. The cartilage was dissected from the bone and frozen sections were prepared and immunostained (FIGS. 14A–D). The level of epitope in the synovial fluid was determined in the synovial lavage fluids by RIA (FIG. 15). The cartilage was stained with the antiserum to localize the fragment (FIG. 14A–D). The epitope was localized to the upper third of the cartilage after stromelysin injection. This staining was blocked by preincubation of the antiserum with Val-Asp-Ile-Pro-Glu-Asn SEQ. ID. NO.: 2 showing that the staining was specific for this epitope. Approximately 80 pmole equivalents of the epitope was found within the synovial lavage. Upon treatment with the inhibitor, there was greater than 90% reduction in the epitope in the cartilage as well as the synovial lavage.

Example 6

Figure 13:
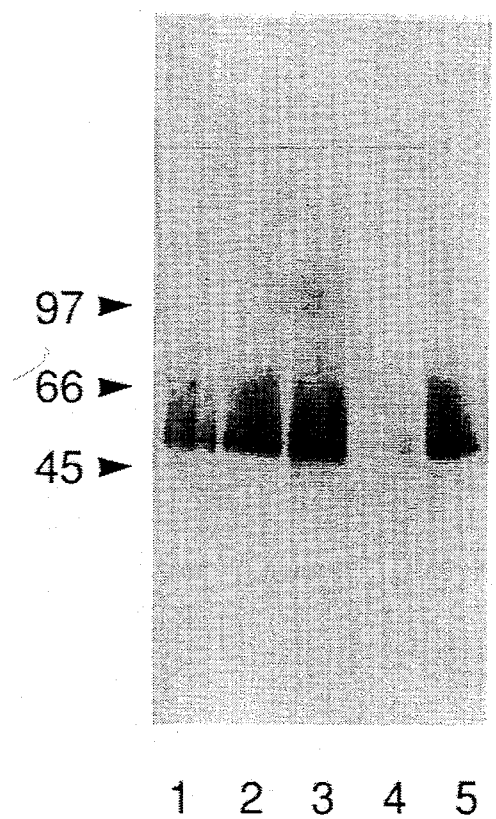
FIG. 13—Western blot is shown which demonstrates aggrecan fragments which are recognized by the anti-VDIPEN antisera can be isolated from human OA cartilege.
Figure 14A:
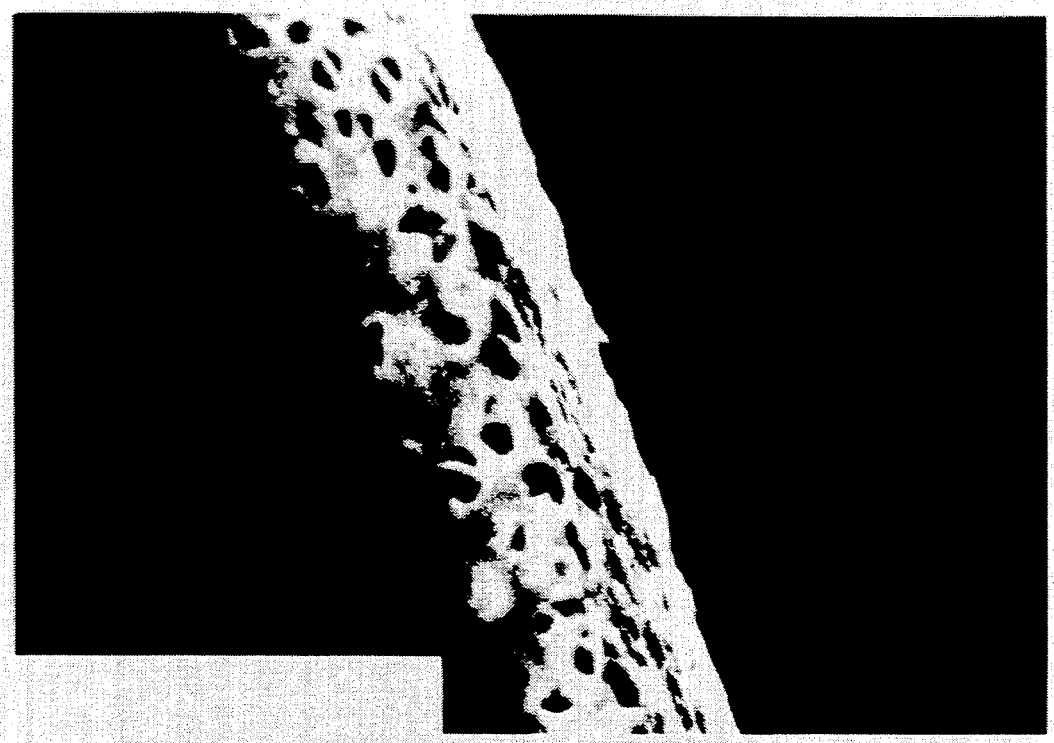
FIG. 14A: Immunofluorescence dam is shown which demonstrates fluorescence in cartilage from a rabbit joint injected intraarticularly with stromelysin (SLN) (test cartilage).
Figure 14B:
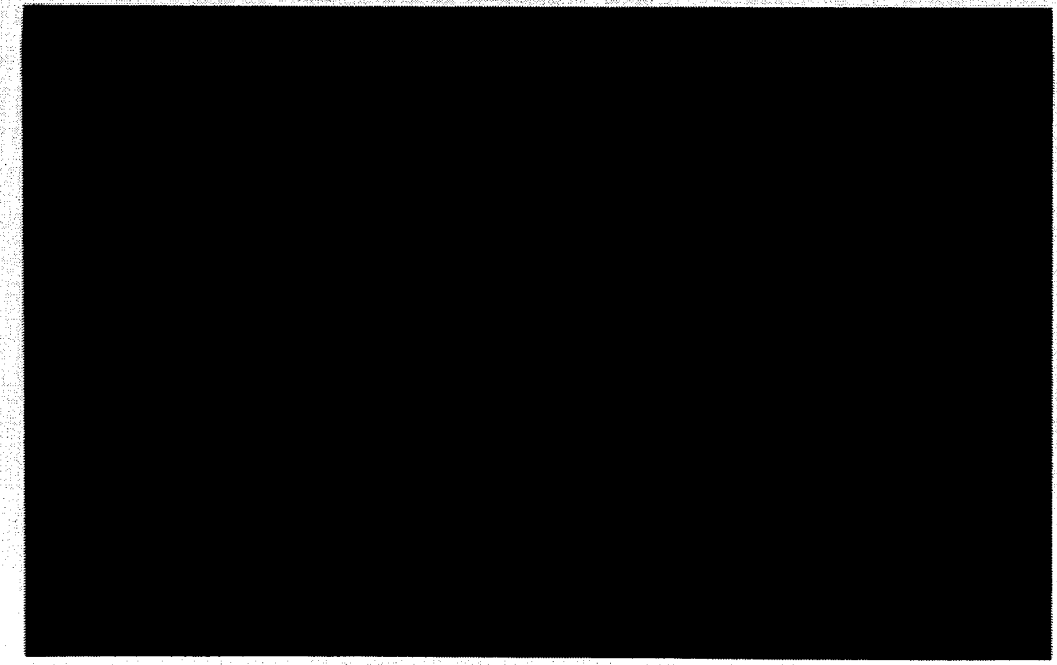
FIG. 14B: Immunofluorescence data is shown which demonstrates control fluorescence in cartilage from a rabbit joint not injected with SLN which was contralateral to that depicted in FIG. 14A.

Isolation of aggrecan fragment recognized by anti-VDIPEN antisera from human OA cartilage Knee cartilage from 5 patients undergoing total joint replacement surgery was treated with 4M guanidine hydrochloride in protease inhibitors [Kimura and Hascall, supra] to extract aggrecan and aggrecan fragments. The aggrecan fragments which bound to hyaluronic acid were fractionated using a combination of associative and dissociative CsCl density gradient fractionation [Kimura and Hascall, supra]. The fraction with the highest density (bottom one-fourth of the gradient) under associative conditions (A1) was isolated and brought to 4M with guanidine hydrochloride. A second gradient was run on this A1 fraction and the top fourth of the gradient (A1D4) was isolated, dialyzed against water and lyophylized. This A1D4 contains proteins and aggrecan fragments which have the capacity to bind hyaluronic acid. The lyophilized AID4 fraction was resuspended in water and electrophoresed on an SDS-PAGE, transfered to nitrocellulose and probed with the anti-VDIPEN antisera. (FIG. 13). Each of the extracts contained a fragment with a Mr 50,000 which was recognized by the anti-VDIPEN antisera. These fragments are similar in size to those generated by SLN cleavage of aggrecan in vitro (FIG. 15). Together this data suggests that aggrecan fragments with C-termini of Val-Asp-Ile-Pro-Glu-Asn, SEQ. ID. NO.: 2 consitent with stromlysin cleavage, can be isolated from human OA cartilage.

---

What is claimed is:

1. A method of evaluating the efficacy of an inhibitor of stromelysin comprising:
   a) combining a stromelysin substrate containing aggrecan with a stromelysin inhibitor;
   b) reacting combined stromelysin substrate and stromelysin inhibitor of step a) with stromelysin in a reaction mixture for a time sufficient to generate stromelysin-cleaved aggrecan peptide fragments from the substrate, wherein stromelysin cleaves aggrecan at a site between Asn and Phe residues of an aggrecan amino acid sequence comprising Asp Ile Pro Glu Asn Phe Phe Gly Val Gly (SEQ. ID. NO: 4) thereby producing said fragments;
   c) contacting a sample of the reaction mixture with a monospecific antibody which specifically binds to an epitope at a terminus of said stromelysin-cleaved aggrecan peptide fragments, wherein said antibody does not bind to uncleaved aggrecan, for a time sufficient for the antibody to bind said fragments present in said sample;
   d) determining an amount of stromelysin-cleaved aggrecan peptide fragments in said sample bound by the antibody in step c) as a measure of a level of said fragments generated in step b); and,
   e) comparing the level of said fragments measured in step d) to a level of fragments measured in a control assay, wherein stromelysin inhibitor was not combined with the stromelysin substrate, as an indication of the efficacy of the inhibitor.

2. The method of claim 1 wherein the stromelysin substrate containing aggrecan is cartilage of a bone joint.

3. The method of claim 2 wherein the reacting with stromelysin in step b) is by intraarticular injection of stromelysin.

4. The method according to any of claims 1, 2, or 3 wherein the sample of the reaction mixture is a sample of fluid from the reaction mixture or a sample of fluid in contact with the reaction mixture.

5. The method according to any of claims 1, 2, or 3 further comprising washing the stromelysin substrate after the contacting step b), thereby removing stromelysin and inhibitor from contact with the substrate, and wherein the sample of the reaction mixture is a sample of washed substrate.

6. The method of claim 1 wherein the monospecific antibody specifically binds to carboxyl-terminal epitope of an amino-terminal stromelysin-cleaved aggrecan peptide fragment comprising the carboxyl-terminal amino acid sequence Asp Ile Pro Glu Asn (SEQ. ID. NO.: 1) and does not bind to uncleaved aggrecan.

7. An assay for the detection of a presence or amount of stromelysin-cleaved aggrecan peptide fragments in a sample comprising:
   a) forming a mixture of a sample, suspected of containing stromelysin-cleaved aggrecan peptide fragments produced by the cleavage of aggrecan by stromelysin at a site between Asn and Phe residues of an aggrecan amino acid sequence comprising Asp Ile Pro Glu Asn Phe Phe Gly Val Gly (SEQ. ID. NO.: 4), with a monospecific antibody which specifically binds to an epitope at a terminus of said stromelysin-cleaved aggrecan peptide fragments, wherein said antibody does not bind to uncleaved aggrecan, for a time sufficient for the antibody to bind said fragments present in said sample;
   b) adding to the mixture a labelled probe comprising a labelled stromelysin-cleaved aggrecan peptide fragment which binds to said antibody; and
   c) measuring an amount of labelled probe bound by said antibody as an indication of the presence or amount of stromelysin-cleaved aggrecan peptide fragments in the sample.

8. The method of claim 7 wherein the monospecific antibody specifically binds to a carboxyl-terminal epitope of an amino-terminal stromelysin-cleaved aggrecan peptide fragment comprising the carboxyl-terminal amino acid sequence Asp Ile Pro Glu Asn (SEQ. ID. NO.: 1) and does not bind to uncleaved aggrecan.

9. The method of claim 1 wherein the monospecific antibody specifically binds to amino-terminal epitope of a carboxy-terminal stromelysin-cleaved aggrecan peptide fragment comprising the amino terminal amino acid sequence Phe Phe Gly Val Gly Gly (SEQ. ID. NO.: 5) and does not bind to uncleaved aggrecan.

* * * * *